US009181523B1

(12) United States Patent
Ganuza et al.

(10) Patent No.: US 9,181,523 B1
(45) Date of Patent: Nov. 10, 2015

(54) METHOD OF TREATING BACTERIAL CONTAMINATION IN A MICROALGAE CULTURE WITH PH SHOCK

(71) Applicant: Heliae Development, LLC, Gilbert, AZ (US)

(72) Inventors: Eneko Ganuza, Phoenix, AZ (US); Anna Lee Tonkovich, Gilbert, AZ (US)

(73) Assignee: Heliae Development LLC, Gilbert, AZ (US)

(*) Notice: Subject to any disclaimer, the term of this patent is extended or adjusted under 35 U.S.C. 154(b) by 24 days.

(21) Appl. No.: 14/585,129

(22) Filed: Dec. 29, 2014

(51) Int. Cl.
C12N 1/12 (2006.01)
A61K 36/02 (2006.01)
C12R 1/89 (2006.01)
A01G 33/00 (2006.01)

(52) U.S. Cl.
CPC . C12N 1/12 (2013.01); A61K 36/02 (2013.01); C12R 1/89 (2013.01); A01G 33/00 (2013.01)

(58) Field of Classification Search
None
See application file for complete search history.

(56) References Cited

U.S. PATENT DOCUMENTS

| 3,444,647 | A | 5/1968 | Takahashi |
| 3,955,318 | A | 5/1976 | Hulls |
| 4,253,271 | A | 3/1981 | Raymond |
| 4,432,869 | A | 2/1984 | Groeneweg |
| 8,478,444 | B2 | 7/2013 | Fuxman et al. |
| 8,759,073 | B2 | 6/2014 | Wang |
| 2008/0220486 | A1 | 9/2008 | Weiss |
| 2010/0297714 | A1 | 11/2010 | Ju |
| 2012/0178123 | A1 | 7/2012 | Rosen |
| 2013/0210122 | A1 | 8/2013 | Wang |
| 2014/0142331 | A1 | 5/2014 | Behrens |
| 2014/0263039 | A1 | 9/2014 | Horst |

FOREIGN PATENT DOCUMENTS

| CN | 1218830 A | 6/1999 |
| CN | 1544612 | 11/2004 |
| CN | 101684447 | 3/2010 |
| GB | 1493480 A | * 11/1977 |

OTHER PUBLICATIONS

Maeda, M.; Taga, N. "Alkalotolerant and Alkalophilic Bacteria in Seawater" Marine Ecology—Progress Series 2, Mar. 31, 1980, pp. 105-108. doi:10.3354/meps002105.*
Vasseur, C.; Rigaud, N.; Hebraud, M.; Labadie, J., "Combined Effects of NaCl, NaOH, and Biocides (Monolaurin or Lauric Acid) on Inactivation of Listeria monocytogenes and Pseudomonas spp." Journal of Food Protection, 2001, 64(9), 1442-1445 (abstract only).*
Yeung, P.S.M and Boor K.J. "Effects of Acid Stress on Vibrio parahaemolyticus Survival and Cytotoxicity", Journal of Food Protection, 2004, 67(7), 1328-1334.*
Williams, R. "pKa Values" pKa Data Compilation <URL: http://research.chem.psu.edu/brpgroup/pKa_compilation.pdf>, archived Nov. 15, 2013, 33 pages.*
Alabama "Useful pKa values" CHEM531 handout, <URL: http://bama.ua.edu/~kshaughn/ch531/531-handouts/pKa-values.pdf> archived Nov. 19, 2012, 1 page.*
Aqion "pH tables—pH of organic acids", <URL:http://www.aqion.de/site/192#acids_pH>, Mar. 2004 (archived Apr. 26, 2004), 4 pages.*
Becker, C.W. "Large-scale Cultivation" Microalgae: Biotechnology and Microbiology, Cambridge Studies in Biotechnology 10, 1994, chapter 10, pp. 152-153 only.*
Asensi, et al., "Bactericidal Effect of ADP and Acetic Acid on Bacilus subtilis," Current Microbiologyo vol. 34 (1997) pp. 61-66.
Basso, et al., "Ethanol Production in Brazil: the industrial process and its impact on yeast fermentation," Bernardes, M.A.S. (Ed) Biofuel Production—Recent Developments and Prospects. 1st Edition Published online CCBY-NC-SA 3.0 license 1530, pp. 85-100.
Bhatnagar et al., "Renewable Biomass Production by Mixotrophic Algae in the Presence of Various Carbon Sources and Wastewaters," Applied Energy, 88, 2011, pp. 3425-3431.
Denicola, et al., "A review of diatoms found in highly acidic environments," Hydrobiologia, Aug. 2000 vol. 433 Issue 1-3 pp. 111-122.
Fraise, et al., "The antibacterial activity and stability of acetic acid," Journal of Hospital Infection, vol. 84, Issue 4, Aug. 2013 pp. 329-331.
Garcia et al., "Mixotrophic Growth of the Microalga Phaeodactylum Tricornutum Influence of Different Nitrogen and Organic Carbon Sources on Productivity and Biomass Composition," Process Biochemistry, 40, 2005, pp. 297-305.
Higgins, et al., "Effects of Escherichia coli on Mixotrophic Growth of Chlorella minutissima and Production of Biofuel Precursors," PLoS One 9(5): e96807, Published May 7, 2014.
Liang, et al., "Utilization of acetic acid-rich pyrolytic bio-oil by microalga Chlamydomonas reinhardtii: Reducing bio-oil toxicity and enhancing algal toxicity tolerance," Bioresource Technology vol. 133 Apr. 2013 pp. 500-506.
Nalewajko, et al., "Effects of pH on growth, photosynthesis, respiration and copper tolerance of three Scenedesmus strains," Environmental and Experimental Botany vol. 37 Issues 2-3 Jun. 1997 pp. 153-160.
Nalewajko, et al., "Photosynthesis of Algal Cultures and Phytoplankton Following an Acid pH Shock," Journal of Phycology Jun. 1989 vol. 25 Issue 2 pp. 319-325.
Olaveson, et al., "Effects of Acidity on the growth of two Euglena species," Hydrobiologia Aug. 2000 vol. 433 Issue 1-3 pp. 39-56.
Qiao, et al., "Short-term effects of acetate and microaerobic conditions on photosynthesis and respiration in chlorella sorokiniana gxnn 01 (chlorophyta)," Journal of Phycology Aug. 2012 vol. 48 Issue 4 pp. 992-1001.

(Continued)

Primary Examiner — Rosanne Kosson
Assistant Examiner — Aaron J Kosar
(74) Attorney, Agent, or Firm — Justin Kniep; Len Smith; Heliae Development LLC

(57) ABSTRACT

Methods of treating contamination, particularly bacterial contamination, in an open culture of microalgae with organic carbon are described herein. The methods comprise reducing the pH of a culture for a period of time and then raising the pH of the culture, wherein the culture comprises the presence of a first acid and the culture is contacted with a second acid to reduce the culture pH from a first pH value to a second pH value. The culture is maintained at the second pH value for at least 5 minutes before the culture pH is raised from the second pH value by contact with a base.

20 Claims, No Drawings

(56) References Cited

OTHER PUBLICATIONS

Rai, et al., "Response of growth and fatty acid compositions of chlorella pyrenoidosa under mixotrophic cultivation with acetate and glycerol for bioenergy application," Biomass and Bioenergy Nov. 2013 vol. 58 pp. 251-257.
Ren, et al., "A new lipid-rich microalga *Scenedesmus* sp. strain R-16 isolated using Nile red staining: effects of carbon and nitrogen sources and initial pH on the biomass and lipid production," Biotechnology for Biofuels 2013 6:143.
Round, et al., "The Diatoms: Biology and Morphology of the Genera," Cambridge University Press 1990 p. 13.
Wang, et al., "Inhibition of ciliates by acidified alga *Chlorella vulgaris* fluid," Fisheries Science Jul. 2005 vol. 24 No. 7 pp. 20-22 ISSN 1003-1111 (translation).
Zhigang, et al., "Studies on Killing *Euplotes* Sp. and *Oxyrrhis* Sp. in the Culture Liquid of Marine Unicellular Algae," Journal of Zhanjiang Fisheries College Dec. 1990 vol. 10 No. 2 pp. 36-41 (English Abstract).
Chakraborty, et al., "Impact of salinity and pH on phytoplankton community in a tropical freshwater system: an investigation with pigment analysis by HPLC," Journal of Environmental Monit. vol. 13(3) 2011 pp. 614-620.
De Swaaf, "Docosahexaenoic acid production by the marine alga *Crypthecodinium cohnii*," Thesis, Apr. 7, 2003, 135 pages.
Camburn, et al., "Diatoms of Low-alkalinity Lakes in Northeastern United States," Apr. 14, 2000, various excerpts, 26 pages.
Lanannan, F., et al. Effect of Conway Medium and f/2 Medium on the growth of six genera of South China Sea Marine Microalgae, Bioresource Technology (2013), doi: http://dx.doi.org/10.105/j.biortech.2013.03.006, 27 pages.

\* cited by examiner

METHOD OF TREATING BACTERIAL CONTAMINATION IN A MICROALGAE CULTURE WITH PH SHOCK

BACKGROUND

Growth of microalgae phototrophically in outdoor open systems subjects the culture of microalgae to multiple challenges not faced by the higher cost closed fermentation systems, such as but not limited to larger loss of gases at the liquid/gas interface and contamination by a variety of microorganisms. Airtight fermentation systems offer better contamination control for heterotrophic systems, thus lending such systems to become the primary production method for many commercial microalgae products. However, fermentation systems are costly to install and operate, and light is limited supply to support a meaningful photosynthetic activity necessary for some algal products.

With the high cost of commercial fermentations systems, methods to achieve the higher growth rates of closed heterotrophic systems have been investigated using the lower cost open systems through mixotrophic cultivation. However, using organic carbon in an open culture has created challenges to the survival of microalgae due to the level of contamination that results.

While contamination exists in open phototrophic microalgae cultures, the introduction of organic carbon results in not only an increased amount of contamination, but also different contaminating organisms than those found in phototrophic cultures. The differences in the contaminating organisms include, but are not limited to, different sizes and rates of replication. For example, contamination in phototrophic cultures primarily comprise predatory organisms such as rotifers, while cultures with organic carbon experience more bacterial contamination. Therefore, the methods traditionally used for contamination control in open phototrophic cultures have not been found to be effective due to these differences, and more effective methods need to be developed to control contamination in open cultures containing organic carbon.

SUMMARY

In one non-limiting embodiment of the invention, a method of culturing microalgae comprises: preparing an open culture with organic carbon in a first bioreactor comprising bacteria and a population of selected microalgae in the presence of a growth sustaining amount of a first acid and a first pH value in the range of 5.5-10.5, the first acid comprising an acid with a pKa value in water in the range of 0-12; contacting the culture with a second acid, wherein a substantial portion of the second acid is made up of at least one acid other than the first acid, such that the pH of the culture is reduced to a second pH value greater than 0 and equal to or less than the pKa value of the first acid; maintaining the culture at the second pH value for a period of at least 5 minutes; and contacting the culture with a base, such that the pH of the culture is raised above the pKa value of the first acid.

In some embodiments, the steps of contacting the culture with a second acid, maintaining the culture at a second pH, and contacting the culture with a base may be repeated. In further embodiments, the steps may be repeated at least two times. In additional further embodiments, the steps may be repeated 2-14 days after the culture pH is raised using the base.

In some embodiments, the first acid may provide a source of organic carbon to the microalgae sufficient for mixotrophic or heterotrophic growth. In some embodiments, the first acid may be present in a primarily dissociated form at the first pH. In some embodiments, the first acid comprises at least one selected from the group consisting of acetic acid, pyruvic acid, propionic acid, palmitic acid, and malic acid. In further embodiments, the first acid may be acetic acid and a concentration of acetate in the culture is maintained at a level less than 7.5 g/L during the culturing.

In some embodiments, the second acid may comprise an acid with a pKa in water of less than −2. In some embodiments, the second acid may comprise at least one from the group consisting of sulphuric acid, hydrochloric acid, and muriatic acid. In some embodiments, the base may comprise at least one from the group consisting of sodium hydroxide, potassium hydroxide, and calcium hydroxide.

In some embodiments, the culture may be maintained at the second pH value for about 5 to 210 minutes. In some embodiments, the culture may be maintained at the second pH value for about 5 to 15 minutes. In some embodiments, the culture may be maintained at the second pH value for about 15 to 60 minutes.

In some embodiments, the first pH may be in the range of 6.5-8.5. In some embodiments, the second pH value may be in the range of 3-4.

In some embodiments, the method may further comprise concentrating the culture in the range of 2-25% solids prior to contacting the culture with the second acid. In some embodiments, the culture may further comprise separating at least a portion of the bacteria from the microalgae, and removing the separated bacteria from the culture prior to contacting the culture with the second acid.

In some embodiments, the cell dry weight density of the culture may be 0.5-5 g/L prior to contacting the culture with the second acid. In some embodiments, the culture may be diluted to a cell density less than or equal to 2 g/L after the culture pH is raised with the base.

In some embodiments, the microalgae may comprise green algae. In some embodiments, the microalgae may comprise at least one green algae selected from the group consisting of *Chlorella* and *Chlamydomonas*.

DETAILED DESCRIPTION

Definitions

The term "microalgae" refers to unicellular algae, cyanobacteria, diatoms, and dinoflagelattes.

The term "productivity" refers to the measure of the microalgae growth rate through cell division and metabolite accumulation, and the term "productive life" refers to the active cell division and metabolite accumulation in live microalgae cells.

The term "areal productivity" or "areal growth rate" refers to the cell dry weight mass of microalgae produced per unit land area per day. An example of such rate is grams per square meter per day ($g/m^2$ d) which is the grams of dry weight microalgae biomass produced per $m^2$ of the reactor area per day.

The term "volume productivity" or "volumetric growth rate" refers to the cell dry weight mass of microalgae produced per unit culture volume per day. An example of such a unit is g/L d (grams per liter per day) which is the grams of dry weight microalgae biomass produced in each liter of the culture per day.

The terms "mixotrophic" and "mixotrophy" refer to culture conditions in which light and organic carbon are utilized by the microalgae as energy sources, and inorganic carbon and organic carbon are utilized by the microalgae as carbon sources.

The terms "phototrophic" and "phototrophy" refer to culture conditions in which light is utilized by the microalgae as an energy source and inorganic carbon (e.g., carbon dioxide, carbonate, bi-carbonate) is utilized by the microalgae as a carbon source.

The terms "heterotrophic" and "heterotrophy" refer to culture conditions in which organic carbon is utilized by the microalgae as both the energy and carbon source.

The term "open culture with organic carbon" refers to conditions of a microalgae culture where the culture comprises microalgae in the presence of an organic carbon source, and is subject to infiltration of contaminating organisms.

The term "axenic" describes a culture of microalgae that is entirely free of all other contaminating organisms.

Overview

A microalgae culture may be any suitable culture where microalgae growth and multiplication is the target of the cultivation activity, the method described herein may be applied to such a microalgae culture. The inventors have found that the presence of an organic carbon source in an open culture of microalgae provides conditions more suitable for the contaminating microorganisms, particularly bacteria, to thrive in such mixotrophic or heterotrophic conditions than in a phototrophic culture of microalgae which does not include a supply or residual concentration of organic carbon. Therefore the inventors have found that the trade-off associated with the increased growth in an open culture with organic carbon is the loss of axenic conditions. Such contaminating microorganisms in a microalgae culture have been found to negatively affect the microalgae through: competition for nutrients (e.g., nitrates, phosphates, trace metals, organic carbon), consumption of available gases (e.g., oxygen, carbon dioxide), clumping of microalgae that reduces availability to light and nutrients, attachment to the microalgae cells, and lysing the microalgae cell walls. When the contaminating microorganism are not controlled or the negative effects are not mitigated, the culture of microalgae may experience a reduction in the productive culture life, reduced yield of microalgae biomass, inhibition of microalgae cell division, a reduction in formation of a targeted high value metabolite (e.g., lipids, proteins, pigments), or potentially death of the entire microalgae culture. Such conditions where contamination is not controlled may lead to or contribute to the death of many or all of the microalgae cells in a matter of hours or days.

Methods known in the art of controlling bacterial contamination in a culture of microalgae include operation under sterile conditions, treatment with antibiotics, ultraviolet (UV) sterilization of culture media, treatment with herbicides, genetic modification of microalgae to increase robustness of the cell or resistance to specific treatments, and treatment with oxidizing agents (e.g., ozone, chlorine, hydrogen peroxide). While these methods are known to provide varying levels of effectiveness, these methods have drawbacks when applied to commercial scale open culture with organic carbon.

For example, operating a commercial scale bioreactor (i.e., 500,000 liters or more) under axenic conditions with sufficient illumination for mixotrophic culturing would be technologically impractical due to the systems needed to maintain sterility and supply access to light in a closed culture without even considering the complications that an open culture would create, and may be economically prohibitive for most products available from microalgae. The use of biocides, antibiotics, and genetic modification may be technologically effective at treating bacteria contamination, but also limit the available end products from the microalgae due to the makeup of the substances added or changes to the microalgae cells. The use of oxidizing agents may negatively affect the growth of microalgae as much as the bacteria, and thus the microalgae may not survive multiple treatments that would likely be necessary over the life of a commercial scale culture.

Methods have been developed to control contaminating microorganisms (e.g., bacteria, fungi, rotifers, protozoans, zooplankton) in an open phototrophic culture. However, the methods that are known to control contaminating microorganisms in phototrophic cultures of microalgae, such as high salinity conditions (10-60 g/L) and sonication, have been shown to be ineffective in treating the bacterial contamination in an open culture with organic carbon. High salinity treatments have not been found to produce a sufficient effect on the bacteria in order to improve the microalgae culture growth, longevity, or health in an open culture with organic carbon; and sonication was found to be ineffective on bacteria cells, which are smaller than the predatory contaminating organisms (e.g., rotifers) typically targeted with such a sonication method in phototrophic cultures. Therefore a new approach was needed for controlling bacterial contamination in an open culture with organic carbon which is able to control bacteria but not harm the microalgae when applying a single treatment, a continuous treatment, or multiple treatments over the life of a microalgae culture at a commercial scale.

Methods of periodically shifting the pH up or down in a culture outside of the optimal range for bacteria culturing are also known in the art for controlling contamination, particularly in phototrophic culture conditions or wastewater treatment applications. Lowering the culture pH to acidic conditions or raising the culture pH to basic conditions may negatively affect some bacteria by creating an environment that is suboptimal for their survival. However, relying on the effect of a suboptimal pH to kill bacteria may take an hour or longer, and after a certain period of time the suboptimal pH environment may also negatively affect the microalgae. Therefore any method that raises or lowers the culture pH to a level outside of the optimal culturing range for a species of microalgae will have to take into account the duration that a microalgae species can tolerate before being negatively affected. The risk of negatively affecting the microalgae also demonstrates the need for a faster acting method for controlling bacteria contamination to reduce the risk of reduced microalgae growth, biomass yield, or metabolite formation.

The anti-bacterial properties of acetic acid are generally known in the art, and have been found to have an increased effectiveness against some bacteria at a low pH (i.e., a pH value at or below the acid dissociation constant pKa value of 4.7 in water). At a pH above the pKa value acetate and associated hydrogen ions (+) are transferred across the material membrane through the acetate proton symport, resulting in acetate within the bacteria cell. While not intending to be bound by an particular theory, the inventors postulate that at pH values equal to or below the pKa value the undissociated acetic acid, which is lipophilic when protonated, may transport through the membrane of a bacteria cell by simple diffusion, resulting in a lowering of the intracellular pH of the bacteria cell from approximately neutral to acidic and the formation of acetate and associated hydrogen ions (+) within the bacteria cytoplasm through dissociation. This lowering of the bacterial intracellular pH results in the death of the bacteria cell. Lowering the pH of a solution comprising acetic acid to the pKa value or lower also results in the formation of acetate through dissociation. Additionally, acetic acid is less polar than acetate and therefore is more permeable to the lipidic cell membrane, which leads to the formation of a residual concentration of acetate in the solution (i.e., culture media).

While some microalgae may use acetate or acetic acid as a carbon source, the inventors determined that too much acetate can also be toxic to microalgae and thus each species of microalgae has an acetate tolerance limit. The higher tolerance limit of microalgae to acetate and undissociated acetic acid, as compared to bacteria, may be attributable to microalgae having a thicker cell wall than bacteria and the presence of differentiated organelles and a nucleus. However, the indiscriminate use of acetic acid or lowering the pH in the presence of acetic acid to treat a microalgae culture contaminated with bacteria may negatively affect the bacteria, but the microalgae may also be negatively affected if the residual acetate concentration formed is above the tolerance limit of the microalgae.

These structural and tolerance differences between prokaryotic bacteria and microalgae may be exploited to the advantage of the microalgae if other factors are taken into account. Therefore, factors that should be taken into account for the use of acetic acid as a treatment to control contaminating bacteria in a microalgae culture include: A) the pH of the culture, B) the pH tolerance of the microalgae, C) the amount of time the culture spends at a pH at or below the pKa value of acetic acid, D) the amount of acetate in the culture, and E) the acetate tolerance of the microalgae species. Similar factors may also warrant consideration in an open culture with an organic carbon or presence of an acid other than acetic acid. Thus a calculated approach using these factors was developed to successfully treat bacterial contamination in an open culture with organic carbon multiple times over the life of the microalgae culture.

The methods developed comprise an efficient way of treating contaminating bacteria in an open culture with organic carbon in a short time frame that minimizes the impact on the microalgae. These methods leverage the benefits of both a shift of the pH to acidic conditions that are suboptimal for bacterial survival and the lowering of the intracellular pH of a bacteria cell through the diffusion of a weak organic acid through the bacterial cell membrane.

Some embodiments of the method comprise the use of a first acid and a second acid in an open culture with organic carbon to achieve the described benefits. The first acid may be a weak organic acid that dissociates at low pH values to provide the contamination control function of diffusion through the bacteria cell membrane for lowering of the bacterial intracellular pH level. The second acid may be a strong acid that is different from the first acid, which provides the function of lowering the pH from the culturing pH level to a level that is both suboptimal for the survival of bacteria and to a level equal to or below the pKa of the first acid to facilitate dissociation of the first acid. After a duration as low as 5 minutes the pH may be raised using a base to within a range that is optimal for culturing the microalgae for biomass or metabolite production.

The use of the first and second acids provides the dual effects on bacteria not present in typical contamination treatment methods using a single acid, and increases the efficiency in treating the contaminating bacteria by increasing the likelihood of killing the bacteria in a shorter time frame. In one non-limiting example, an open culture with organic carbon using acetic acid (pKa of 4.7) as the organic carbon source in the microalgae culture would provide the presence of the first acid (i.e., acetic acid) for the method. Lowering the pH with a strong acid (i.e., a second acid with a pKa in water less than −2), such as hydrochloric acid, that is different from the first acid (i.e., acetic acid) would prevent the excess formation of acetate exceeding the tolerance limit of the microalgae when the pH is lowered to a level equal to or below the pKa of acetic acid. Using a further amount of acetic acid (i.e., first acid) in a single acid method, instead of a different second acid, to lower the pH may produce an acetate concentration in the culture that is detrimental to the microalgae.

The use of two acids also allows the dual effects of lowering the intracellular pH and creating acidic culture conditions to efficiently attack contaminating bacteria in a short time frame (e.g., as little as 5 minutes) to reduce the risk of any detrimental effect to the microalgae. The reduced impact on the microalgae of the described methods also allows for the methods to be applied multiple times to the same culture of microalgae with a lower risk of harming the microalgae (e.g., microalgae cell death, slowing the growth rate, reducing biomass accumulation, reducing the accumulation of metabolites).

The presence of an organic carbon source functioning as the first acid in combination with a different second acid makes the described methods more effective for treating contaminating bacteria in an open culture with organic carbon, and distinguishes the methods from a typical single acid (i.e., acetic acid or hydrochloric acid only) application for pH shift used to treat contamination in a phototrophic culture of microalgae. Phototrophic cultures do not utilize an organic carbon source, and therefore may not have the presence of the first acid, such as acetic acid, that may penetrate the bacteria and lower the intracellular pH upon contact of the culture with the second acid to lower the pH. Lowering the pH in a phototrophic culture with only acetic acid (i.e., the first acid) would risk producing an acetate concentration in the culture that is detrimental to the microalgae.

Also, lowering the pH in a phototrophic culture with only the second acid only (i.e., a strong acid different from acetic acid) would create the single effect of making the pH suboptimal for bacteria survival, and would require a longer time duration to produce the desired results of live bacteria reduction. For example, lowering the culture pH with hydrochloric acid (HCl) to a pH below 4 would completely dissociate the HCl and therefore would not be available in the protonated state to penetrate the bacterial cell wall and lower the intracellular pH. The longer time duration required to negatively affect the bacteria also risks creating an environment which negatively affects the microalgae. Therefore, the describe methods provide increased effectiveness in treating bacterial contamination, particularly in open cultures with organic carbon.

While not all bacteria found in a microalgae culture may be affected by the described methods, examples of bacteria that have been shown to be both harmful to microalgae and affected by the described methods are *Vampirovibrio chlorellavorus* and *Cytophaga* sp. Thus it is likely that bacteria with similar physiological characteristics to *Vampirovibrio chlorellavorus* or *Cytophaga* sp., such as make up and permeability of the cytoplasmic membrane, the strength of the cell wall, and resiliency of the respiratory cycle, would be affected in a similar negative manner by the described methods.

Embodiments of Methods for Treating Bacterial Contamination in a Microalgae Culture In one embodiment, a selected population of microalgae in an open culture with organic carbon may be prepared in a first bioreactor. The culture of microalgae may be prepared in non-axenic conditions which further comprise bacteria.

In some embodiments, the selected population of microalgae may comprise natural or wild type microalgae. In some embodiments, the selected population of microalga may comprise genetically or transgenically modified microalgae. In some embodiments, the selected population of microalgae may comprise green algae. Green algae refers to eukaryotic algae containing chlorophyll and capable of photosynthetic activity. In some embodiments, the selected population of microalgae comprises algae in the divisions Chlorophyta and Charophyta. In further embodiments, selected population of microalgae may comprise at least one selected from the group consisting of *Chlorella* and *Chlamydomonas*. *Chlorella* and *Chlamydomonas* are preferable types of microalgae for the methods due to the ability to grow mixotrophically using acetic acid as an organic carbon source and the ability to tolerate culture conditions of a pH below 4 for a short time period without negatively affecting the microalgae. For example, *Chlorella* has an optimal growth pH in the range of 6.5-8.5, can tolerate a pH of 3.5 for up to 3 hours without detriment, and demonstrate productive growth at a pH of 10.5. *Chlamydomonas* has an optimal growth pH in the range of 6.5-8.5, and is known to tolerate a pH as low as 2.5 for short time periods.

In some embodiments, the culture of microalgae may further comprise a growth sustaining amount of a first acid, wherein a "growth sustaining amount" refers to an amount of the first acid which does not inhibit the growth of the microalgae. One non-limiting example of a growth sustaining amount of a first acid may comprise 0.1-5 g/L of acetate or acetic acid. In some embodiments, the culture of microalgae may further comprise an amount of a first acid below the tolerance limit of the microalgae. One non-limiting example of an amount of a first acid below the tolerance limit of the microalgae may be less than 7.5 g/L of acetate in a culture of *Chlorella*. In some embodiments, the culture of microalgae may further comprise an amount of a first acid that contributes to the growth of the microalgae. In some embodiments, the first acid may be an organic acid. In further embodiments, the first acid may be an organic acid with a pKa value in water in the range of −2 to 12 (i.e., weak organic acid). In some embodiments, the first acid may be an acid with a pKa value in water in the range of 0-12.

In some embodiments, the culture of microalgae may receive the first acid through a pH auxostat system. A pH auxostat microbial cultivation technique couples the addition of medium containing organic carbon, such as acetic acid, to pH control. The pH level represents the summation of the production of different ionic species and ion release during carbon and nutrient uptake, therefore the pH level can move either up or down as a function of growth of the microalgae. As the pH drifts from a given set point, fresh medium is added to bring the pH back to the set point. The medium feed will keep the residual nutrient concentration in balance with the buffering capacity of the medium. The pH set point may be changed depending on the microalgae present in the culture at the time. The rate of medium addition is determined by the buffering capacity and the feed concentration of the limiting nutrient and not directly by the pH set point as in a traditional auxostat. Through the use of the pH auxostat system, the pH controls nutrient concentration (e.g., acetic acid) within the culture indirectly.

The culture of microalgae may be prepared at a first pH value that is within a range that does not inhibit growth of the microalgae. In some embodiments, the culture of microalgae may be prepared at a first pH value within a range that is optimal for the growth of the microalgae. In some embodiments, the range of the first pH may comprise a pH value in the range of 5.5-10.5. In some embodiments, the range of the first pH may comprise a pH value in the range of 6-9. In some embodiments, the range of the first pH may comprise a pH value in the range of 6.5-8.5. In some embodiments, the range of the first pH may comprise a pH value in the range of 7-8. In some embodiments, the range of the first pH may comprise a pH value in the range of 7-7.5. In some embodiments, the range of the first pH value may comprise 1.1 to 2.25 times the pKa value of the first acid. In some embodiments, the range of the first pH value may comprise 1.25-2 times the pKa value of the first acid. In some embodiments, the range of the first pH value may comprise 1.25-1.75 times the pKa value of the first acid. In some embodiments, the range of the first pH value may comprise 1.5-1.75 times the pKa value of the first acid. In some embodiments, the range of the first pH value may comprise 1.5-1.6 times the pKa value of the first acid.

In some embodiments, the pH culture is lowered to a second pH value by contacting the culture with a pH reducing means. The culture of microalgae may be contacted with a second acid, wherein a substantial portion of the second acid is made up of at least one acid other than the first acid, such that the pH of the culture is reduced to a second pH value below the first pH value. The term "a substantial portion" refers to at least 50% of the total composition, and preferably is at least 60%, at least 70%, at least 80%, or at least 90% of the total composition. In some embodiments, the second pH value may be less than the first pH value. In some embodiments, the second pH value may be equal to or less than the pKa value of the first acid for pKa values above 0. In some embodiments, the second pH value may be in the range of 1-5. In some embodiments, the second pH value may be in the range of 1.5-5. In some embodiments, the second pH value may be in the range of 2-4.75. In some embodiments, the second pH range may be in the range of 2.5-4. In some embodiments, the second pH value may be in the range of 3-4.

The culture of microalgae may be maintained at the second pH value for a period of time of at least 5 minutes. In some embodiments, the culture of microalgae may be maintained at the second pH value for a period of time of at least 15 minutes. In some embodiments, the culture may be maintained at the second pH value for about 5 to 210 minutes. In some embodiments, the culture may be maintained at the second pH value for about 5 to 15 minutes. In some embodiments, the culture may be maintained at the second pH value for about 15 to 30 minutes. In some embodiments, the culture may be maintained at the second pH value for about 30 to 60 minutes. In some embodiments, the culture may be maintained at the second pH value for about 60 to 90 minutes. In some embodiments, the culture may be maintained at the second pH value for about 90 to 120 minutes. In some embodiments, the culture may be maintained at the second pH value for about 120 to 180 minutes. In some embodiments, the culture may be maintained at the second pH value for about 180-210 minutes.

In some embodiments, the pH culture is raised by contacting the culture with a pH raising means. In some embodiments, following the end of the time period at the second pH value, the culture of microalgae may be contacted with a base to raise the pH of the culture of microalgae. In some embodiments, the pH of the culture of microalgae is raised to within the first pH value range. In some embodiments, the pH of the culture of microalgae is raised to within 40% of the first pH value. In some embodiments, the pH of the culture of microalgae is raised to within 30% of the first pH value. In some embodiments, the pH of the culture of microalgae is raised to within 20% of the first pH value. In some embodiments, the pH of the culture of microalgae is raised to within 10% of the first pH value. In some embodiments, the pH of the culture of microalgae is raised to greater than the pKa value of the first acid.

In some embodiments, the method may be repeated multiple times for a single culture of microalgae for a plurality of treatments over the life of the culture. In some embodiments, repeating the method may comprise contacting the culture comprising an amount of the first acid at a first pH value range with a second acid an additional time to lower the pH of the culture to a second pH value equal to or below the pKa of the first acid for pKa values above 0, maintaining the culture at the second pH value for a period of at least 5 minutes, and contacting the culture with a base to raise the pH above the pKa value of the first acid. In some embodiments, the first acid, first pH value, second acid, second pH value, period of time, or base of the subsequent treatments may be the same as in a previous treatment. In some embodiments, the first acid, first pH value, second acid, second pH value, period of time, or base of the subsequent treatments may be different from a previous treatment. In some embodiments, the method may be repeated automatically following the passing of a scheduled time period. In some embodiments, the method may be repeated 2-14 days after the culture pH is returned to within the first pH value range, preferably within 2-10 days, and most preferably repeated within 2-7 days.

In some embodiments, the method may comprise treating the whole culture of microalgae continuously or at discrete times by contacting the entire culture with the second acid and base. In further embodiments, a portion of the prepared microalgae culture may be treated by removing a first fraction of the culture from the first bioreactor comprising a first acid and a first pH value range. In some embodiments, the first fraction may comprise at least 10% of the culture. In some embodiments, the first fraction may comprise 10-25% of the culture. In some embodiments, the first fraction may comprise 25-50% of the culture. In some embodiments, the first fraction may comprise 50-60% of the culture. In some embodiments, the first fraction may comprise 60-70% of the culture. In some embodiments, the first fraction may comprise 70-80% of the culture. In some embodiments, the first fraction may comprise 80-90% of the culture. In some embodiments, the first fraction may comprise 90-95% of the culture. The removal may also be termed a partial harvest or split of the culture. The first fraction of the culture may be contacted with a second acid, wherein a substantial portion of the second acid is made up of at least one acid other than the first acid, such that the pH of the first fraction of the culture is reduced to a second pH value equal to or below the pKa value of the first acid. The first fraction of the culture may be maintained at the second pH value for a period of at least 5 minutes, and then contacted with a base such that the pH of the first fraction culture is raised to above the pKa value of the first acid. In some embodiments, the first fraction of the culture may be returned to first bioreactor wherein the first fraction of the culture is mixed with the culture in the first bioreactor.

In some embodiments, the steps of separating the first fraction of the culture, treating the first fraction of the culture, and returning the first fraction of the culture may be repeated multiple times (i.e., at least two times) to facilitate a plurality of treatments of the same culture of microalgae. In some embodiments, the steps of separating the first fraction of the culture, treating the first fraction of the culture, and returning the first fraction of the culture may be repeated on a continuous basis. In some embodiments, the steps of separating the first fraction of the culture, treating the first fraction of the culture, and returning the first fraction of the culture may be repeated 0-72 hours after the first fraction of the culture is returned to the first bioreactor, and preferably repeated within 0-60 hours, 0-48 hours, 12-48 hours or 24-36 hours.

In some embodiments, the first fraction of the culture may be separated from the culture in the first bioreactor by removal means comprising any means known in the art, such as but not limited to draining, scooping, or pumping the fraction from the first bioreactor. In some embodiments, the first fraction of the culture may be treated with the described method in a second bioreactor, piping, or fluid flow conduit. In some embodiments, the first fraction of the culture may be returned to the first bioreactor through piping or a fluid flow conduit. In some embodiments, the first fraction of the culture treated by the described method may not return to the first bioreactor, and instead go to a bioreactor other than the first bioreactor or to a container for further processing. In some embodiments, a portion of the first fraction may be returned to the first bioreactor, and a portion may go to a bioreactor other than the first bioreactor or to a container for further processing.

Organic carbon sources in an open culture may comprise organic carbon suitable for growing microalgae mixotrophically or heterotrophically such as, but not limited to: acetate, acetic acid, ammonium linoleate, arabinose, arginine, aspartic acid, butyric acid, cellulose, citric acid, ethanol, fructose, fatty acids, galactose, glucose, glycerol, glycine, lactic acid, lactose, maleic acid, maltose, mannose, methanol, molasses, peptone, plant based hydrolyzate, proline, propionic acid, ribose, sacchrose, partial or complete hydrolysates of starch, sucrose, tartaric, TCA-cycle organic acids, thin stillage, urea, industrial waste solutions, yeast extract, and combinations thereof. The organic carbon source may comprise any single source, combination of sources, and dilutions of single sources or combinations of sources.

In some embodiments, the first acid may comprise at least one acid from the group consisting of acetic acid (pKa of about 4.7), pyruvic acid (pKa of about 2.5), propionic acid (pKa of about 4.9), palmitic acid (pKa of about 4.7), and malic acid (pKa of about 3.4). In some embodiments, the first acid may comprise acetic acid at a concentration of 10-80%, 10-70%, 10-60%, 10-50%, 10-40%, or 10-30%. In some embodiments, the first acid may comprise acetic acid and the step of maintaining the culture at the second pH value for a period of at least 5 minutes and the concentration of acetate in the culture is maintained at a level of 7.5 g/L or less, preferably at a level of 5 g/L or less, and most preferably at a level of 2.5 g/L or less during the culturing of the microalgae. In some embodiments, the first acid may be excreted into the culture by the microalgae. In some embodiments, the first acid may be a combination of at least two acids. In some embodiments, the first acid may provide a source of organic carbon to the microalgae sufficient for mixotrophic or heterotrophic growth. In some embodiments, the first acid may improve the growth of the microalgae by providing a source of energy and carbon utilized as such by the microalgae.

In some embodiments, the first acid may be present in its primarily dissociated form at the first pH value range. In some embodiments, the first acid may be in a primarily undissociated form and capture protons when the pH is lowered to the second pH value. In some embodiments, the first acid may diffuse through the cell membrane of the bacteria when the second pH value is equal to or less than the pKa value of the first acid. In some embodiments, acetic acid may diffuse through the cell membrane of the bacteria when the second pH value is equal to or less than the pKa value of the acetic acid without forming an acetate concentration in the culture greater than the tolerance of the microalgae species (e.g., greater than 7.5 g/L in a culture of *Chlorella*). In some embodiments, the intracellular pH of the bacteria may decrease as the first acid diffuses through the cell membrane of the bacteria. In some embodiments, the intracellular pH value of the bacteria may decrease when the second pH value is equal to or less than the first acid pKa value.

In some embodiments, the second acid may comprise an acid with a pKa in water of less than −2 (i.e., strong acid). In some embodiments, the second acid may comprise at least one from the group consisting of sulfuric acid (pKa of about −3), hydrochloric acid (pKa of about −7), and muriatic acid (about 30% concentration of HCl). In some embodiments, the second acid may be diluted to create a solution with a low pH (e.g., 1-3) that may be used to contact the culture and reduce the culture pH. In some embodiments the concentration of the second may comprise a concentration in the range of 1-5M, preferably 2-5 M, and most preferably 2-4 M. In some embodiments, the second acid may be a combination of at least two acids.

In some embodiments, the base may comprise at least one selected from the group sodium hydroxide, potassium hydroxide, and calcium hydroxide. In further embodiments, the sodium hydroxide may be at a concentration in the range of 1-5M, preferably 2-5 M, and most preferably 2-4M. In some embodiments, the addition of the base may cause the culture pH level to rise to above the first pH value range or a desired pH value within the first pH value range and necessitate correcting the pH level with the addition of an acid to lower the culture pH to a desired value within the first pH value range. In some embodiments, the base may comprise a combination of at least two bases.

In some embodiments, the bacteria may comprise a detectable amount of *Vampirovibrio chlorellavorus*. In some embodiments, the bacteria may comprise a deleterious amount of *Vampirovibrio chlorellavorus*. In some embodiments, the bacteria may comprise a detectable amount of *Cytophaga* sp. In some embodiments, the bacteria may comprise a deleterious amount of *Cytophaga* sp.

In some embodiments, the method may further comprise determining a first live bacteria count of the culture before contact with the second acid, and determining a second live bacteria count of the culture after the culture pH is raised. In some embodiments, the live bacteria count may be quantified by aerobic colony forming units (CFU). In some embodiments, a live bacteria count may be determined using methods known in the art such as plate counts, plates counts using Petrifilm available from 3M (St. Paul, Minn.), spectrophotometric (turbidimetric) measurements, visual comparison of turbidity with a known standard, direct cell counts under a microscope, cell mass determination, and measurement of cellular activity. Live bacteria counts in an open culture with organic carbon may range from $10^4$ to $10^9$ CFU/mL. In some embodiments, the second live bacteria count may be reduced by at least 1 log within 48 hours or less as compared to the first live bacteria count. In some embodiments, the second live bacteria count may be reduced by 1-4 logs within 48 hours or less as compared to the first live bacteria count. The difference in the first and second live bacteria count values may be maintained for at least 48 hours after the culture pH is raised, and in some embodiment for at least 48-60, 60-72, 72-84, or 84-96 hours.

Some bacteria in the microalgae culture may attach to the cell wall of the microalgae, eventually lysing the cell wall of the microalgae and killing the microalgae. Thus visual observation of the bacteria attaching to the microalgae under a microscope is a useful indicator of the health of the microalgae culture and the percentage of microalgae cells that have at least one bacteria cell attached out of the total microalgae cells in the culture (i.e., % of bacterial attachment) may be used as an indicator of when to treat the microalgae culture with the described methods and the success of the treatment. An example of bacteria known to attach to microalgae is *Vampirovibrio chlorellavorus*.

In some embodiments, the described methods may be used as a rescue treatment for a microalgae culture when the % of bacterial attachment is high (i.e., about 50% or higher) and still maintain viability of the microalgae. In some embodiments, the described methods may be used a preventative treatment for a microalgae culture when the % of bacterial attachment is low (i.e., less than 50%) and still maintain microalgal growth. After treatment with the described methods, further attachment of the bacteria may be prevented, as well as reversing the attachment state of the previously attached bacteria.

In some embodiments, the described methods may reduce the % of bacterial attachment in the microalgae culture by at least 50% in 24 hours or less after the culture pH is returned to within the first pH value range. In some embodiments, the described methods may reduce the % of bacterial attachment in the microalgae culture to less than 5% in 48 hours or less after the culture pH is returned to within the first pH value range. In some embodiments, the described methods may prevent the % of bacterial attachment from increasing for at least 24 hours, preferably for at least 48 hours, and more preferably for at least 96 hours after the culture pH is returned to within the first pH value range.

In some embodiment, the culture may be monitored for a live bacteria count and the method may be carried out or repeated when the live bacteria count of the culture reaches a threshold level of $10^4$, $10^5$, $10^6$, $10^7$, or $10^8$ CFU/mL. In some embodiments, the culture may be monitored for attachment to the microalgae cell wall and the method may be carried out or repeated when the attachment of bacteria to the microalgae cell wall reaches a threshold level. In some embodiments, the method may be carried out or repeated when the level of attachment of bacteria to the microalgae cell wall reaches at least 10%, at least 20%, at least 30%, at least 50%, at least 60%, at least 70% at least 80%, or at least 90%. In some embodiments, the method may be carried out or repeated when the level of attachment of bacteria to the microalgae cell wall is 10-90%. In some embodiments, the method may be carried out or repeated when the level of attachment of bacteria to the microalgae cell wall is 10-30%. In some embodiments, the method may be carried out or repeated when the level of attachment of bacteria to the microalgae cell wall is 30-50%. In some embodiments, the method may be carried out or repeated when the level of attachment of bacteria to the microalgae cell wall is 50-80%. In some embodiments, the method may be carried out or repeated when the level of attachment of bacteria to the microalgae cell wall is 80-90%.

In addition to the reduction in bacteria attachment and live bacteria count, the clumping of microalgae cells in the culture as visually observed under a microscope may also be reduced after the culture is returned to within the first pH value range. A difference in the color of a microalgae culture treated with the described methods as compared to an untreated culture may also be visually observed, with the treated culture displaying a vibrant green color and the untreated culture displaying a brown color as bacteria proliferate and kill the microalgae.

In some embodiments, the described methods may further comprise analyzing the culture before contact with the second acid to determine a first live bacteria population composition, and analyzing the culture after the culture pH is returned to within the first pH value range to determine a second live bacteria population composition. The live bacteria population make up analysis may be conducted using DNA sequencing analysis, Quantitative Polymerase Chain Reaction (qPCR), Next Generation Sequencing, microarrays, fluorescent in situ hybridization FISH), flow cytometry coupled with digital imaging and image recognition, and metagenomic sequencing. In some embodiments, the second live bacteria population composition may have less *Vampirovibrio chlorellavorus* bacteria than the first live bacteria population composition. In some embodiments, the second live bacteria population composition may have less *Cytophaga* sp. bacteria than the first live bacteria population composition. In some embodiments, the live bacteria population composition may be monitored, and the method may be carried out or repeated when a detectable level of an undesirable bacteria, such as but not limited to *Vampirovibrio chlorellavorus* or *Cytophaga* sp., is measured.

In some embodiments, the described methods may further comprise concentrating the culture of microalgae prior to contacting the culture with the second acid. In some embodiments, the culture of microalgae may be concentrated in the range of 2-25% solids. In some embodiments, the culture of microalgae may be concentrated in the range of 20-25% solids. In some embodiments, the culture of microalgae may be concentrated in the range of 15-20% solids. In some embodiments, the culture of microalgae may be concentrated in the range of 10-15% solids. In some embodiments, the culture of microalgae may be concentrated in the range of 5-10% solids. In some embodiments, the culture of microalgae may be concentrated in the range of 2-5% solids. Concentration of the microalgae culture may be conducted by any method known in the art such as, but not limited to centrifugation, filtration, and electrocoagulation means. Concentration of the culture may improve the handling of the culture during treatment with the second acid and base. Concentrating the culture may also increases the efficiency of the described methods by reducing the volume of the microalgae culture and thus requiring a smaller volume of the second acid to be used to lower the pH value of the culture. In some embodiments, at least a portion of the bacteria and microalgae of the culture may be separated by particle density, particle size, or surface charge prior to contact with the second acid, thereby reducing the amount of bacteria in the culture to treat.

In some embodiments, the described methods may further comprise transferring the entire culture from the first bioreactor to a second bioreactor after the culture is contacted with the second acid. In some embodiments, the described methods may further comprise transferring the entire culture from the first bioreactor to a second bioreactor after the culture is contacted with the base. Such transfers may occur when inoculating a larger sized bioreactor in a commercial operation with staged bioreactors of increasing size, or splitting the culture into multiple bioreactors to maintain an optimal culture density. The act of inoculation comprises any method known in the art for introducing microalgae into a culture medium.

In some embodiments, microalgae may be cultured in any suitable means for culturing microalgae. The first and second bioreactors may comprise any suitable open culturing vessel such as, but not limited to, a raceway pond, a flat panel bioreactor, a bag bioreactor, a bubble column bioreactor, a tank, and a trough. The first and second bioreactors may be open bioreactors, disposed indoors, disposed outdoors, or covered. In some embodiments, the first and second bioreactors may be the same. In some embodiments, the first and second bioreactors may be different.

In some embodiments, the described methods may further comprise culturing the microalgae in phototrophic conditions after the culture is treated with the described methods. In some embodiments, the methods may further comprise culturing the microalgae in mixotrophic conditions after the culture is treated with the described methods. In some embodiments, the methods may further comprise culturing the microalgae in heterotrophic conditions after the culture has been treated with the described methods.

In some embodiments, the methods further comprise supplying the culture of microalgae with photosynthetically active radiation (PAR). Non-limiting examples of PAR are light in the wavelength spectral range of 400-700 nanometers, and light wavelengths capable of use by a photosynthetic organism for photosynthesis.

In some embodiments, the culture of microalgae comprises a volume of 1,000-500,000, 10,000-100,000, or 30,000-50,000 liters. For a commercial stage culturing operation the culture of microalgae may comprise a volume of 100,000-500,000 liters.

In some embodiments, the described methods may further comprise adding a probiotic culture of bacteria to the culture of microalgae after the culture pH is raised above the pKa of the first acid. In some embodiments, the described methods may further comprise adding nutrients (e.g., nitrates, phosphates, trace metals) or new culture media to the culture of microalgae after the culture pH is raised above the pKa of the first acid.

In some embodiments, the described methods may further comprise removing foam from the culture after the culture pH is raised above the second pH value. The foam may be removed from any foam removing means known in the art such as, but not limited to, a foam aspirator device, a foam fractionation device, an anti-foam spray down, and a weir.

In some embodiments, a cell dry weight density of the culture may be in the range of 0.5-5, 1-4, 1-3, or 1-2 g/L prior to contacting the culture with the second acid. In some embodiments, the culture may be diluted to a cell dry weight density of less than or equal to 2 g/L after the culture pH raised is above the pKa of the first acid. The dilution may correspond to inoculating a larger bioreactor and adding culture medium to the increase the culture volume to achieve a target density (e.g., 1 g/L, 2 g/L, 3 g/L, 4 g/L) for continued growth of the microalgae.

In some embodiments, the described methods may comprise continuing growth of the microalgae culture for at least 48 hours longer than the growth in an untreated control. In some embodiments, the described methods may extend the productive life of the microalgae in the culture at least twice as long as the productive life of microalgae in an untreated control. It has been observed with mixotrophic cultures of *Chlorella* receiving acetic acid as the organic carbon source that an untreated culture will die (i.e., crash) after about 7 days, while a culture treated with the described methods once will continue the productive life of the culture for about 14 days, and a culture treated more than once with the described methods may continue the productive life of the culture for 20 or more days.

EXAMPLES

Embodiments of the invention are exemplified and additional embodiments are disclosed in further detail in the following Examples, which are not in any way intended to limit the scope of any aspects of the invention described herein.

Example 1

Cultures of *Chlorella* sp. were prepared to determine the effect on growth yield of different concentrations of sodium acetate (sodium salt of acetic acid) on mixotrophically cultured *Chlorella*. 100 mL volume cultures were prepared in 250 mL flasks, and cultured at a temperature of 25° C., a shaking frequency of 100 rpm, and a light intensity of 100 μM photon/m$^2$ s for 7 days (168 hours). The cultures were inoculated into two times BG-11 culture media at a cell density of 1.12 g/L. The different treatments of sodium acetate consisted of concentrations of 0, 2.5, 5, 7.5, 10, 20, 30, and 40 g/L. Samples were taken every 24 hours to measure the cell dry weights (g/L) of the cultures. The results of the experiment are presented in Table 1.

TABLE 1

| Time (h) | Cell dry weights (g/L) of treatments by Concentration of Sodium Acetate (g/L) | | | | | | | |
|---|---|---|---|---|---|---|---|---|
| | 0 | 2.5 | 5 | 7.5 | 10 | 20 | 30 | 40 |
| 0 | 0.12 ± 0.00 | 0.12 ± 0.00 | 0.12 ± 0.00 | 0.12 ± 0.00 | 0.12 ± 0.00 | 0.12 ± 0.00 | 0.12 ± 0.00 | 0.12 ± 0.00 |
| 24 | 0.20 ± 0.02 | 0.23 ± 0.01 | 0.19 ± 0.06 | 0.17 ± 0.04 | 0.13 ± 0.00 | 0.16 ± 0.02 | 0.14 ± 0.03 | 0.11 ± 0.01 |
| 48 | 0.58 ± 0.04 | 0.85 ± 0.01 | 0.25 ± 0.03 | 0.15 ± 0.02 | 0.16 ± 0.01 | 0.13 ± 0.01 | 0.11 ± 0.02 | 0.09 ± 0.01 |
| 72 | 0.77 ± 0.02 | 1.10 ± 0.05 | 0.55 ± 0.06 | 0.13 ± 0.03 | 0.11 ± 0.03 | 0.12 ± 0.02 | 0.09 ± 0.01 | 0.10 ± 0.04 |
| 144 | 2.56 ± 0.23 | 2.72 ± 0.06 | 1.89 ± 0.19 | 0.10 ± 0.09 | 0.09 ± 0.03 | 0.07 ± 0.00 | 0.08 ± 0.01 | 0.09 ± 0.00 |
| 168 | 3.09 ± 0.03 | 3.23 ± 0.04 | 2.41 ± 0.09 | 0.07 ± 0.00 | 0.00 ± 0.00 | 0.00 ± 0.00 | 0.00 ± 0.00 | 0.00 ± 0.00 |

The results in Table 1 show that the *Chlorella* grew well on 2.5 g/L sodium acetate (0.620 g/L day) and showed positive growth on 5 g/L (0.065 g/L day), but did not show any growth on concentrations of 7.5 g/L and higher. Observations under a microscope also showed that the *Chlorella* on 0 and 2.5 g/L sodium acetate comprised a darker green color than the culture at 5 g/L. The culture that received 2.5 g/L of sodium acetate also reached exponential phase after 48 hours. Thus, the acetate concentration tolerance for *Chlorella* was determined to be low at approximately 7.5 g/L, which may provide a limitation as to the use of acetic acid in a low pH treatment when acetic acid is already present in a growth sustaining amount.

Example 2

An experiment was conducted to investigate the effect on bacteria in a microalgae culture at various pH levels in the presence of a concentration of acetate. A 1.4 liter sample from an open outdoor bioreactor culturing *Chlorella* in mixotrophic conditions comprising acetic acid (i.e., first acid) as the organic carbon source and natural sunlight was divided into 18 flask cultures under aseptic conditions comprising 250 ml. 1.25 ml of 200 g/L concentrated sodium acetate (i.e., sodium salt form of first acid) solution was added to each flask. Next, 10% v/v HCl (i.e., second acid) was used to lower the pH, or 2M NaOH (8 g of sodium hydroxide in solution with 100 ml of purified water) was used to raise the pH of the cultures to test duplicates of the culture pH conditions of 9.5, 8.5, 7.5, 6.5, 5.5, 4.5, 3.5, 2.5, and 1.5. The pH modified cultures were placed on a shaker plate for 15 minutes, and then returned to a culture pH of 7. Samples were then taken to measure live bacteria counts quantified using aerobic colony forming units (CFU) obtained from plate counts utilizing Petrifilm available from 3M (St. Paul, Minn.). The results of the experiment are presented in Table 2.

TABLE 2

| pH | Total bacteria count (CFU) |
|---|---|
| 1.5 | 4.25E+05 ± 7.07E+03 |
| 2.5 | 5.00E+05 ± 7.07E+04 |
| 3.5 | 3.77E+06 ± 3.24E+06 |
| 4.5 | 2.40E+07 ± 2.83E+06 |
| 5.5 | 1.35E+08 ± 3.54E+07 |
| 6.5 | 3.75E+07 ± 4.95E+06 |
| 7.5 | 3.85E+07 ± 9.19E+06 |
| 8.5 | 3.80E+07 ± 1.70E+07 |
| 9.5 | 5.00E+06 ± 0.00E+00 |

The results in Table 2 show that the effect of the acetate concentration on the total live bacteria count at a pH of 5.5 was minimal. At culture pH levels below 5.5 the total live bacteria count dropped rapidly. These results suggest that the effect on the bacteria by the acetate concentration is associated with acetic acid in its undissociated form occurring at pH levels at or below the pKa of 4.7.

Example 3

Axenic cultures of *Chlorella* sp. were prepared for determining the ability of the microalgae to survive a treatment with a low pH solution (i.e., a solution with a pH below the optimal growth range of 6.5-8.5 for *Chlorella* sp.). *Chlorella* sp. growing on an acetic acid/pH-auxostat system comprising approximately 5-10% solids by dry weight was used to form triplicates of a control culture with no treatment at grown at a relatively constant pH of 7.5, and a treated culture in which the pH of the culture was: A) lowered from 7.5 to 3.5 for approximately 15 minutes using a solution of water distilled by a Milli-Q water purification system (Millipore, Bedford, Mass.) with the pH lowered by the addition of 2M of a second acid consisting of hydrochloric acid (HCl) to 2, and then B) raised to 7.5 with addition of a solution containing 2M of a base consisting of sodium hydroxide (NaOH). An Erlenmeyer flask was inoculated with the 100 ml of the prepared *Chlorella* sp. culture at a culture density of approximately 0.5 g/L dry weight using BG-11 culturing medium (trace metals formulation available from University of Texas at Austin Culture Collection of Algae (UTEX) containing 2.5 g/L sodium acetate (sodium salt of acetic acid). Light was also provided 24 h a day with florescent bulbs to create mixotrophic growth conditions at a level of 100 μM photon/m$^2$ s. The cultures were grown for six days (144 hours) in axenic conditions (i.e., without exposure to bacterial contamination) with dry weight samples taken at 0, 48, 96, and 144 hours. The results of the experiment are presented in Table 3.

TABLE 3

| Time (h) | Control cell dry weight (g/L) | pH treated cell dry weight (g/L) |
|---|---|---|
| 0 | 0.50 ± 0.02 | 0.50 ± 0.02 |
| 48 | 0.83 ± 0.02 | 0.75 ± 0.11 |
| 96 | 0.99 ± 0.08 | 0.68 ± 0.02 |
| 144 | 1.13 ± 0.01 | 1.46 ± 0.04 |

The results in Table 3 show that the *Chlorella* sp. cultures treated with the low pH solution for 15 minutes produced comparable dry weights to the untreated control cultures, and confirm that the *Chlorella* are capable of surviving the treatment of lowering the culture pH to 3.5 and can continue to grow after the treatment returns the culture pH to 7.5.

Example 4

To determine the tolerance of *Chlorella* sp. to pH treatment of varying durations the following experiment was performed. Axenic cultures of *Chlorella* sp. growing on an acetic acid/pH-auxostat system were centrifuged and pH treated as described in Example 3 by reducing the pH of the culture to 3.5 for 0, 15, 30, 60 and 180 min, and then returning the culture pH to 7.5 using 2 M NaOH. The resulting culture was inoculated (20% v/v) in BG-11 culture media and fed 2.5 g/L sodium acetate (sodium salt of acetic acid) daily. Erlenmeyer flasks (250 ml) containing 100 ml of microalgae culture were incubated for 144 h at 100 RPM, 25° C. and 100 µM photon/$m^2$ s. The cultures were grown for six days (144 hours) in axenic conditions (i.e., without exposure to bacterial contamination) with cell dry weight samples taken at 0, 24, 48, 72, and 144 hours in order to determine the tolerance of *Chlorella* sp. to the pH treatment duration. The results of the experiment are presented in Table 4.

TABLE 4

| Time | Cell Dry Weight (g/L) of pH treated cultures by duration (min) | | | | |
|---|---|---|---|---|---|
| (h) | 0 | 15 | 30 | 60 | 180 |
| 0 | 1.00 ± 0.14 | 0.81 ± 0.16 | 0.89 ± 0.13 | 0.88 ± 0.14 | 0.95 ± 0.10 |
| 24 | 1.56 ± 0.07 | 1.11 ± 0.16 | 1.12 ± 0.05 | 1.09 ± 0.08 | 1.16 ± 0.03 |
| 48 | 2.45 ± 0.09 | 1.91 ± 0.21 | 2.17 ± 0.01 | 1.81 ± 0.30 | 2.13 ± 0.06 |
| 72 | 2.81 ± 0.04 | 2.69 ± 0.13 | 2.73 ± 0.04 | 2.68 ± 0.07 | 2.26 ± 0.03 |
| 144 | 3.41 ± 0.08 | 3.15 ± 0.01 | 3.21 ± 0.06 | 2.96 ± 0.34 | 3.23 ± 0.25 |

The results in Table 4 show that the *Chlorella* sp. cultures treated with the low pH (3.5) solution produced comparable dry weights to each other and the control regardless of the duration of the treatment (up to 180 min). Therefore a delay in pH treating *Chlorella* sp. cultures for longer than 15 min should not impair the viability of the microalgae.

Example 5

The following experiment was performed to study the effect of different degrees of pH treatment and treatment duration on the growth of *Chlorella* sp. cultures. Axenic cultures of *Chlorella* sp. growing on an acetic acid/pH-auxostat system were centrifuged pH treated as described in Example 3 by reducing the pH of the culture to 1.2, 2.5, or 3.5, for 15 minutes using 2 M HCl, and then returning the pH to 7.5 using 2 M NaOH. One culture was did not have the pH lowered, and instead maintained the culture pH at 7.5 as an untreated control. The resulting cultures were inoculated (20% v/v) in BG-11 culture media and fed 2.5 g/L sodium acetate (sodium salt of acetic acid) daily. Erlenmeyer flasks (250 ml) containing 100 ml were incubated for 144 h at 100 RPM, 25° C. and 100 µM photon/$m^2$ s. The cultures were grown for seven days (144 hours) in axenic conditions (i.e., without exposure to bacterial contamination) with dry weight samples taken at 0, 24, 48, 72, and 144 hours in order to determine the tolerance of *Chlorella* sp. to the pH treatment duration. The results of the experiment are presented in Table 5.

TABLE 5

| Time | Cell Dry Weight (g/L) of pH treated cultured by pH level applied to the treatment | | | |
|---|---|---|---|---|
| (h) | 7.5 | 3.5 | 2.5 | 1.2 |
| 0 | 0.83 ± 0.05 | 0.79 ± 0.01 | 0.77 ± 0.01 | 0.73 ± 0.01 |
| 24 | 1.21 ± 0.10 | 1.18 ± 0.01 | 1.19 ± 0.03 | 1.08 ± 0.04 |
| 92 | 3.20 ± 0.07 | 2.88 ± 0.07 | 3.14 ± 0.14 | 2.91± 0.26 |
| 164 | 4.36 ± 0.04 | 4.00 ± 0.28 | 4.30 ± 0.08 | 3.97 ± 0.30 |

The results in Table 5 show that the *Chlorella* sp. cultures could be pH treated as low as 1.2 for 15 min and survive with comparable subsequent growth to the cultures treated at a pH of 2.5 and 3.5. The results also show that *Chlorella* sp. cultures to be pH treated with a target pH of 3.5 for 15 min should not be impaired as far as viability or productive life of the culture if too much of the second acid is added or the pH is not tightly controlled and the pH drops as low as 1.2.

Example 6

Cultures of *Chlorella* sp. growing on an acetic acid/pH-auxostat system were prepared for determining the ability to survive a treatment with a low pH solution after centrifugation, which may be important to processing the algae and/or in providing additional protection against contamination. The *Chlorella* sp. used in this experiment consisted of samples from open, outdoor cultures which also contained contaminating bacteria. The performance of three different treatments were evaluated including centrifuged, centrifuged and pH treated, and a non-centrifuged and non-pH treated control. The centrifuge step (12,000 g for 15 min) resulted in a concentrated paste of *Chlorella* sp. comprising approximately 5-10% solids by dry weight. The paste was used to inoculate the centrifuged treatment at an initial cell concentration of 0.5 g/L. The pH treatment was applied to the centrifuged paste as described in Example 3 to lower the culture pH to 3.5 using 2M HCl. The cultures were then incubated for 15 minutes at 100 rpm shaking before raising the pH back to 7.5 using 2M NaOH. The control treatment consisted of a sample from the outdoor culture diluted to match an initial cell concentration of 0.5 g/L and was maintained at a culture pH of about 7.5. All treatments were inoculated in triplicate flasks with the 100 ml of the prepared *Chlorella* sp. culture at a culture density of approximately 0.5 g cell dry weight/L using BG-11 culturing medium. Both cultures also included 10 g/L sodium acetate (sodium salt of acetic acid), which acts primarily as a carbon source but also modulates pH of the culture and may assist in contamination control. Light was also provided to create mixotrophic growth conditions. The cultures were grown for five days (120 hours) in non-axenic conditions with dry weight samples taken at 0, 48, and 120 hours. The results of the experiment are presented in Table 6.

TABLE 6

| Time (h) | Control cell dry weight (g/L) | Centrifuged cell dry weight (g/L) | Centrifuged and pH treated cell dry weight (g/L) |
|---|---|---|---|
| 0 | 0.59 ± 0.19 | 0.47 ± 0.01 | 0.47 ± 0.01 |
| 48 | 2.81 ± 0.17 | 2.88 ± 0.04 | 2.74 ± 0.26 |
| 120 | 3.87 ± 0.07 | 4.07 ± 0.01 | 4.03 ± 0.02 |

The results in Table 6 show that the centrifuged *Chlorella* sp. cultures treated with the low pH solution for 15 minutes produced comparable dry weights to the control and centrifuged only cultures, and confirms that *Chlorella* cultured in non-axenic conditions are capable of surviving the low pH treatment and can continue to grow after both centrifugation and pH treatment. Visual observation under a microscope also showed that after 5 days the pH treated culture had fewer colonies of live bacteria than the control and centrifuge only cultures.

Example 7

Cultures of *Chlorella* sp. were prepared for determining the ability to survive a treatment with a low pH solution after centrifugation and additional experimental steps were taken to study the results of such combination treatment on bacterial contamination in the treated cultures. The *Chlorella* sp. used in this experiment comprised samples from open, outdoor cultures cultured in mixotrophic conditions with acetic acid as the organic carbon source which also contained contaminating $1.1 \times 10^7$ CFU bacteria. The performances of three different culture conditions were evaluated including (1) culture centrifugation; (2) centrifugation and pH treatment (similar to as performed in Example 6); and (3) a non-centrifuged and non-pH treated control. The centrifuge treatment consisted of a culture centrifuged for 12,000 g for 5 minutes resulting in a *Chlorella* sp. paste comprising approximately 5-10% solids by cell dry weight. The paste was inoculated into the centrifuged treatments to match an initial cell concentration of 1 g/L. The paste was also pH treated as described in Example 3 reducing the pH to 2.5 using 2M HCl, incubated for 15 minutes (25° C., 100 RPM shaking), and raising the pH to 7.5 using 2 M NaOH. The non-centrifuged, non-pH treated control consisted of a sample from the outdoor culture inoculated at pH 7.5 to match an initial cell concentration of about 0.5 g/L. All treatments were incubated in triplicate 250 ml Erlenmeyer flasks containing 100 ml of the prepared *Chlorella* sp. culture at a starting culture density of approximately 1 g/L cell dry weight using BG-11 culturing medium. The organic carbon source used for the culture was sodium acetate (sodium salt of acetic acid) at a concentration of 2.5 g/L, added daily. 100 μM photon/m² s of light was also provided to create mixotrophic growth conditions. The cultures were monitored for six days (144 hours) in non-axenic conditions with dry weight samples taken at 0, 48, 96, and 144 hours. Live bacteria contamination samples were taken at 0 and 48 hours, and quantified using aerobic colony forming units (CFU) obtained from plate counts utilizing Petrifilm available from 3M (St. Paul, Minn.). A bacteria to microalgae ratio was also quantified using guava flow cytometry. The results of the experiment are presented in Tables 7, 8, and 9.

TABLE 7

| Time (h) | Control cell dry weight (g/L) | Centrifuge treated cell dry weight (g/L) | Centrifuge and pH treated cell dry weight (g/L) |
| --- | --- | --- | --- |
| 0 | 1.10 ± 0.07 | 0.96 ± 0.02 | 0.95 ± 0.03 |
| 48 | 2.81 ± 0.06 | 2.63 ± 0.20 | 2.39 ± 0.06 |
| 120 | 3.33 ± 0.16 | 3.12 ± 0.22 | 3.40 ± 0.09 |

TABLE 8

| Time (h) | Control bacteria (CFU/mL) | Centrifuge treated bacteria (CFU/mL) | Centrifuge and pH treated bacteria (CFU/mL) |
| --- | --- | --- | --- |
| 0 | $1.30\,10^8 \pm 1.0\,10^7$ | $5.27\,10^7 \pm 1.17\,10^7$ | $1.23\,10^6 \pm 5.77\,10^4$ |
| 48 | $2.64\,10^8 \pm 2.52\,10^7$ | $1.5\,10^8 \pm 3.61\,10^7$ | $1.57\,10^7 \pm 2.89\,10^6$ |

TABLE 9

Bacteria to Algae Ratio (Guava Flow Cytometry bacteria to microalgae ratio)

| Time (h) | Control | Centrifuged | Centrifuged & pH-treated |
| --- | --- | --- | --- |
| 0 | 1.61 ± 0.39 | 1.24 ± 0.77 | 0.07 ± 0.01 |
| 48 | 1.12 ± 0.26 | 0.98 ± 0.44 | 0.01 ± 0.00 |
| 120 | 1.23 ± 0.18 | 0.90 ± 0.41 | 0.13 ± 0.01 |

The results in Table 7 show that the *Chlorella* sp. cultures treated with the combined centrifuged and low pH solution for 15 minutes produced comparable dry weights to the control and centrifuge treated cultures, and confirms that the *Chlorella* in non-axenic conditions are capable of surviving the low pH treatment and can continue to grow after treatment. The results in Table 8 show a difference in the live bacteria count between the centrifuge and pH treated, control, and centrifuge treated cultures, with the culture receiving the pH treatment resulting in an almost two log reduction in the live bacteria count compared to the control.

The results were confirmed by the flow cytometry analysis of bacteria to microalgae ratio, which Table 9 shows the centrifuged and pH treated culture having a ratio of one order of magnitude lower than centrifuged and control cultures. Visual observation under a microscope showed that after 5 days the centrifuged and pH treated culture had fewer colonies of live bacteria than the centrifuged and control cultures. Regarding culture longevity, it was observed that after 5 days the control and centrifuge treated cultures were no longer growing, while the centrifuged and pH treated culture continued to grow for over 8 days thus indicating that the pH treatment may extend the productive life of a *Chlorella* culture by reducing the amount of live bacteria that may compete with or harm the *Chlorella*. While centrifuge treating the culture of microalgae provides some benefit in reducing the bacteria, the combined effect of centrifugation with low pH treatment provides an increased benefit for reducing bacteria and extending the productive life of the microalgae.

Example 8

Cultures of *Chlorella* sp. growing on an acetic acid/pH-auxostat system were prepared for determining the ability to survive a treatment with a low pH solution in the same manner as Example 7 and for demonstrating the relationship between culture longevity and exemplary treatment methods according to aspects of the invention. Flasks was inoculated with the 60 ml of the prepared *Chlorella* sp. culture at a culture density of approximately 1 g/L dry weight using BG-11 culturing medium. The organic carbon source used for the culture was sodium acetate (sodium salt of acetic acid) at a concentration of 2.5 g/L, added daily. 100 μM photon/m² s of light was also provided to create mixotrophic growth conditions. The cultures were incubated for 5 days (120 hours) in non-axenic conditions with dry weight samples taken at 0, 48, and 96 hours. Live bacteria count samples were taken at 0 and 48 hours, and quantified using aerobic colony forming units (CFU) obtained from plate counts utilizing Petrifilm available from 3M (St. Paul, Minn.). The results of the experiment are presented in Tables 10 and 11.

TABLE 10

| Time (h) | Control cell dry weight (g/L) | Centrifuge treated cell dry weight (g/L) | Centrifuge and pH treated cell dry weight (g/L) |
|---|---|---|---|
| 0 | 1.00 ± 0.02 | 0.86 ± 0.02 | 0.90 ± 0.01 |
| 48 | 2.20 ± 0.09 | 1.81 ± 0.02 | 2.07 ± 0.13 |
| 120 | 2.96 ± 0.03 | 2.63 ± 0.03 | 3.76 ± 0.33 |

TABLE 11

| Time (h) | Control bacteria (CFU/mL) | Centrifuge treated bacteria (CFU/mL) | Centrifuge and pH treated bacteria (CFU/mL) |
|---|---|---|---|
| 0 | $3.50\ 10^6 \pm 3.0\ 10^6$ | $1.93\ 10^5 \pm 5.86\ 10^4$ | $9.00\ 10^4 \pm 4.36\ 10^4$ |
| 48 | $4.93\ 10^7 \pm 3.36\ 10^7$ | $5.70\ 10^6 \pm 4.53\ 10^6$ | $6.70\ 10^6 \pm 3.61\ 10^5$ |

The results in Table 10 show that the *Chlorella* sp. cultures treated with the low pH solution for 15 minutes produced comparable dry weights to the control and centrifuge treated cultures, and confirms that the *Chlorella* in non-axenic conditions are capable of surviving the low pH treatment and can continue to grow after treatment. The results in Table 11 showed a difference in the live bacteria count between the control and the centrifuge or centrifuge and pH treated cultures, with the centrifuge treatment resulting in an almost one log reduction in the live bacteria count and the centrifuge and pH treatment resulting in more than a one log reduction.

The bacteria count results were confirmed by flow cytometry analysis, which showed that the bacteria to microalgae ratio after 96 h of incubation were 0.84±0.06 for the control, 0.99±0.11 for the centrifuged, and 0.12±0.25 for the centrifuged and pH treated. Regarding culture longevity, it was observed that after about 4.5 days the control and centrifuge treated cultures were no longer growing, while the centrifuged and pH treated culture continued to grow thus indicating that the pH treatment contributed to extending the productive life of a *Chlorella* culture by reducing the amount of live bacteria that may compete with or harm the *Chlorella*.

Example 9

Cultures of *Chlorella* sp. were prepared for determining the effect on microalgae growth and live bacteria count using acetic acid or hydrochloric acid to reduce the culture pH in a low pH treatment. An outdoor culture of *Chlorella* sp. growing in mixotrophic conditions with BG-11 culture media and using an acetic acid/pH auxostat system (i.e., first acid) to maintain the organic carbon source (acetate) level between 100 and 1000 ppm was split into duplicates of three 400 ml cultures.

The first 400 ml culture was maintained as an untreated control at a pH of about 7.5. The second and third 400 ml cultures were lowered from a pH of about 7.5 to 3.5 for 15 minutes, and then raised back to a pH of 7-7.5 using 5M NaOH. In the second culture the pH was lowered using 20% (v/v) acetic acid (i.e., first acid). In the third culture the pH was lowered using HCl (i.e., second acid) as described in the previous examples. The pH treatments were applied directly to the cultures, without previous concentration of the microalgae or subsequent dilution through inoculation into fresh culture media. All cultures were incubated with shaking at 100 rpm in 5% carbon dioxide and 25° C. 2.5 g/L of sodium acetate (sodium salt of acetic acid) was added daily as the organic carbon source. 100 μM photon/m² s of light was also provided to create mixotrophic growth conditions. The cultures were monitored for 4 days (96 hours with dry weight samples taken at 0, 48, and 96 hours). Live bacteria count samples were taken at 0 and 48 hours, and quantified using aerobic colony forming units (CFU) obtained from plate counts utilizing Petrifilm available from 3M (St. Paul, Minn.). A bacteria to microalgae ratio was also quantified using guava flow cytometry. The results of the experiment are presented in Tables 12, 13, and 14.

TABLE 12

| Time (h) | Control cell dry weight (g/L) | Acetic acid pH treated cell dry weight (g/L) | HCl pH treated cell dry weight (g/L) |
|---|---|---|---|
| 0 | 0.80 ± 0.03 | 0.76 ± 0.00 | 0.80 ± 0.03 |
| 48 | 1.83 ± 0.13 | 1.73 ± 0.04 | 2.54 ± 0.00 |
| 96 | Culture Crash | 3.46 ± 0.09 | 3.78 ± 0.00 |

TABLE 13

| Time (h) | Control bacteria (CFU/mL) | Acetic acid pH treated bacteria (CFU/mL) | HCl pH treated bacteria (CFU/mL) |
|---|---|---|---|
| 0 | $2.00\ 10^6 \pm 1.41\ 10^5$ | $1.40\ 10^5 \pm 2.83\ 10^4$ | $1.85\ 10^5 \pm 7.07\ 10^3$ |
| 48 | $1.04\ 10^8 \pm 1.22\ 10^8$ | $9.00\ 10^6 \pm 8.20\ 10^5$ | $4.91\ 10^6 \pm 5.78\ 10^6$ |

TABLE 14

Bacteria to Algae Ratio (Guava Flow Cytometry)

| Time (h) | Untreated | Acetic acid pH treated | HCl pH treated |
|---|---|---|---|
| 0 | 3.15 ± 0.46 | 0.19 ± 0.02 | 0.15 ± 0.04 |
| 72 | 2.71 ± 0.49 | 0.18 ± 0.01 | 0.13 ± 0.01 |

The results in Table 12 show that the *Chlorella* sp. cultures treated with the low pH solutions for 15 minutes produced comparable dry weights to the control culture, and confirms that the *Chlorella* in non-axenic conditions are capable of surviving the low pH treatment and can continue to grow after treatment with acetic acid or HCl.

The results also showed a higher cell dry weight numbers for the HCl treated culture compared to the acetic acid treated culture, indicating that the treatment using HCl in a culture where acetic acid is already present in a growth sustaining amount may be preferably over the treatment with additional acetic acid to maximize the productivity of the microalgae by avoiding the accumulation of acetate in the culture above the tolerance level of the microalgae.

The results in Table 13 show the difference in the live bacteria count between the control and the pH treated cultures, with the pH treatments resulting in more than one log reduction as compared to the control. The reduction in bacteria in the pH treated cultures is confirmed in the results shown in Table 14.

Regarding culture longevity, it was observed that after about 4 days the control culture was no longer growing, while the pH treated cultures continued to grow thus indicating that the pH treatment may extend the productive life of a *Chlorella* culture by reducing the amount of live bacteria that may compete with or harm the *Chlorella*.

The results also show the effectiveness in treating a culture that has not been concentrated or diluted with a low pH to affect the bacteria population. Treatment without concentration may save time and energy, thereby increasing the overall efficiency of the process.

Example 10

Samples from an open outdoor culture of *Chlorella* sp. growing mixotrophically on acetic acid (i.e., first acid) were used for determining the effect on microalgae growth after pH treating with acetic acid or hydrochloric acid. The culture was operating at a concentration of 1,029 mg/L of acetate (i.e., salt form of first acid) before the pH treatments were applied. In the acetic acid pH treatment, about 60 ml of 20% v/v acetic acid (i.e., first acid) were used to drop the culture pH down to 3.5. The pH treated culture samples were maintained at the culture pH of 3.5 for 15 minutes before returning the culture pH to 7.5 by adding 2 M NaOH. Another culture sample was treated with HCl (i.e., second acid) as described in the previous examples, and a third culture sample was not pH treated to provide a control.

The acetic acid/pH treated culture was compared to the control culture and the HCl/pH treated cultures during a four day incubation period. The pH treatment was applied directly into the culture, without previous concentration or subsequent dilution through inoculation into a fresh media. All cultures were incubated with shaking at 100 rpm in 5% carbon dioxide and 25° C. 2.5 g/L of sodium acetate (sodium salt of acetic acid) was added daily as the organic carbon source. 100 μM photon/m$^2$ s of light was also provided to create mixotrophic growth conditions. The cultures were monitored for 4 days (96 hours with dry weight samples taken at 0, 48, and 96 hours). Residual acetate analyses were carried at the end of the experiment. The growth results of the experiment are presented in Table 15.

TABLE 15

| | Cell Dry Weight (g/L) | | |
|---|---|---|---|
| Time (h) | Untreated | Acetic acid/ pH treated | HCl/pH treated |
| 0 | 0.87 ± 0.01 | 0.80 ± 0.02 | 0.89 ± 0.01 |
| 48 | 1.90 ± 0.11 | 0.78 ± 0.06 | 1.88 ± 0.04 |
| 96 | 2.70 ± 0.00 | 0.89 ± 0.01 | 2.58 ± 0.01 |

The results in Table 15 show that the *Chlorella* sp. culture with the presence of a growth sustaining amount of acetate (i.e., salt form of first acid) that was pH treated with acetic acid (i.e., first acid) did product subsequent growth comparable to the control or HCl treated culture. The HCl treated cultured produced double the microalgae growth after 48 hours and nearly triple the growth after 96 hours. The residual acetate in the culture (9650±150 mg/L) was above the tolerance limit for this strain of *Chlorella* as determined in Example 8 (7500 mg/L sodium acetate), and 5200 mg/L higher than the untreated cultures.

The survival of the HCl/pH treated culture that also had a previously existing growth sustaining presence of acetate (i.e., salt form of first acid) suggests that using an acid (i.e., second acid such as HCl) other than acetic acid to lower the pH during treatment is preferable to the use of acetic acid (i.e., first acid), is instrumental in maintaining the residual acetate concentrations below the acetate tolerance limit of the microalgae. The success of a pH treatment utilizing acetic acid to lower the pH will therefore depend on the buffering capacity of the culture at the time of treatment. Based on the results of this experiment, a preferred embodiment of the pH treatment of a culture with a presence of acetate or acetic acid (i.e., first acid) in a growth sustaining amount is the use of a second acid other than acetic acid, such as hydrochloric acid, to lower the culture pH in order avoid the potential formation of harmful concentrations of acetate.

Example 11

An experiment was conducted to determine if the presence of sodium acetate (sodium salt of acetic acid) in a culture of microalgae increases the effect on the total live bacteria count when the pH is reduced to 3.5. A 2 L sample of a mixotrophic culture of *Chlorella* containing live bacteria was taken from an open raceway pond bioreactor disposed in a greenhouse receiving natural light and acetic acid (i.e., first acid) as the organic carbon source. The 2 L sample was split into equal 1 L cultures in flasks, and incubated at 25° C. and 100 rpm (shaking) for 24 hours to allow metabolization of any residual acetate in the cultures. The two cultures were then blended together and then separated into equal 1 L cultures to ensure homogeneity in the two cultures. The pH of each culture was verified to be 7.5. Sodium acetate (sodium salt of acetic acid) was added to one culture to create the presence of a concentration of 2.5 g/L of acetate as a first acid in the culture, a concentration above the typical operating range of 0.5-1 g/L of acetate. The second culture did not receive sodium acetate in order to serve as a control without the presence of a first acid for comparison purposes. Hydrochloric acid (i.e., second acid) was added to both cultures to lower the pH to 3.5, which is below the pKa value of 4.7 for acetic acid. Samples were taken from both cultures to quantify the initial live bacteria count and subsequent counts using aerobic colony forming units (CFU) obtained from plate counts utilizing Petrifilm available from 3M (St. Paul, Minn.). The results of the experiment are presented in Table 16.

TABLE 16

| | Total live bacteria count (CFU) | |
|---|---|---|
| Time (min) | 0 g/L of Sodium Acetate (control) | 2.5 g/L Sodium Acetate |
| 0 | 3.30E+06 | 5.00E+06 |
| 5 | 1.90E+05 | 8.00E+04 |
| 15 | 1.70E+05 | 4.00E+04 |
| 30 | 3.00E+04 | none detected |
| 60 | 1.60E+05 | 1.00E+03 |
| 180 | 1.00E+03 | 1.00E+03 |

As shown in Table 16, the total live bacteria count for both cultures decreased over time. However, the live bacteria count in the culture with the concentration of 2.5 g/L sodium acetate (i.e., first acid) decreased at a faster rate initially than the control culture, with the effect compounding over time. This accelerated effect on bacteria shown in the data supports the described dual effects provided in a pH treatment method utilizing two acids instead of just a single acid.

After 60 minutes, the live bacteria counts were below detection at 1,000 CFU/ml in the culture with the concentration of 2.5 g/L sodium acetate. After 180 minutes, there was no measureable live bacterium in either of the cultures. These results show that in a culture of *Chlorella* with the presence of sodium acetate (i.e., first acid) and treated with a second acid, had a larger drop in the live bacteria count occurs in the first 15 minutes than a culture lacking the presence of a first acid before treatment with a second acid, and after 60 minutes a 3.5 order of magnitude reduction in live bacteria is achievable with the two acid method.

Example 12

A culture of mixotrophic *Chlorella* sp. using acetic acid/pH auxostat system (i.e., first acid) as the organic carbon source (100-1000 ppm) that had previously received a low pH treatment in a 1,000 liter pond bioreactor by reducing the pH from 7.5 to 3.5 using HCl (i.e., second acid), incubated for 15 minutes, and raising the pH to 7.5 using NaOH was used to determine the effect of a second low pH treatment. A 100 ml sample of the culture of *Chlorella* sp. that had been previously pH treated 7 days prior was determined by observation under a microscope to have an attachment level of *Vampirovibrio chlorellavorus* bacteria to the *Chlorella* of 85%. The culture pH was then reduced from 7.5 to 3.5 using HCl (18%) (i.e., second acid), incubated for 15 minutes at 100 rpm shaking, and the culture pH raised to 7.5 using 4 M NaOH. The culture was monitored and compared to a control from the previously pH treated *Chlorella* culture that did not receive a second pH treatment. Both cultures were fed 2.5 g/L of sodium acetate (sodium salt of acetic acid) daily as an organic carbon source and cultured in mixotrophic conditions as described in the previous examples. Samples were taken every two days to determine the cell dry weight (g/L) of the cultures.

Observations under a microscope on day 4 (96 h) showed that the control culture had reached a bacteria attachment level of 100%, while the culture receiving the second pH treatment was at a bacteria attachment level of about 4.5%. The bacteria attachment in the culture receiving the second pH treatment had been reduced to 0% within 48 hours, and slowly rose to 100% attachment toward the crash of the culture after 48 hours. The results of the experiment are presented in Table 17.

TABLE 17

| Time (h) | Control cell dry weight (g/L) | HCl pH treated cell dry weight (g/L) |
|---|---|---|
| 0 | 1.05 | 1.05 |
| 48 | 2.12 | 2.79 |
| 96 | Crash | 3.87 |
| 144 | Crash | 4.79 |

The results in Table 17 show that the untreated culture died after 48 hours, while the pH treated culture continued to grow. By comparison, the original culture of *Chlorella* that did not receive either the first or second pH treatments lasted about 7 days before a majority of the *Chlorella* showed bacterial attachment to the microalgae cell walls, while the culture that received one pH treatment continued the productive life for approximately 14 days, and the culture that received two pH treatments lasted until day 20 when it was discarded but still comprised indicators that the culture would have been viable for possibly 2-4 additional days or even longer.

Example 13

The following experiment was performed to determine if the pH treatment method could extend the productive life of a culture of microalgae with high levels of bacteria attachment (above 50%). Samples from a culture with high levels of bacteria attachment (approximately 70%) were pH treated and compared to untreated samples from the same culture. A 509 liter sample of a *Chlorella* culture contaminated with bacteria growing outdoors in mixotrophic conditions with natural light and acetic acid/pH-auxostat system running at residual acetate concentration in the range of 100-2500 ppm (i.e., first acid) as the organic carbon source at a pH of about 7.5 in an open 130,000 liter raceway pond bioreactor was transferred to a tote container. Within the tote container, the culture pH was reduced to 3.5 using HCl (37%) (i.e., second acid) and maintained at a pH of 3.5 for 15 minutes. The culture pH was then raised to 8.5 using NaOH and transferred to a first open raceway pond bioreactor filled with 545 liters of BG-11 culture medium (including 0.5 g/L sodium acetate). A 609 liter sample from the same culture in the 130,000 liter bioreactor was transferred to a second open raceway pond bioreactor filled with 545 liters of BG-11 culture medium (including 0.5 g/L sodium acetate) without a pH treatment as a control culture. The first and second open raceway pond bioreactors were both fed 20% v/v acetic acid and 2% w/v sodium nitrate through a pH auxostat system with a set point of pH 7.4, maintained at a temperature of 24±2° C., received paddlewheel agitation at 25 Hz, and received natural sunlight. Both cultures in the first and second open raceway pond bioreactors had an initial culture density of 1.0 g/L cell dry weight. The cultures in the first and second raceway pond bioreactors were monitored for 7 days (168 hours), with cell dry weight (g/L) samples taken every 12 hours. Bacteria to algae ratios were also estimated periodically using guava flow cytometry. Live total bacteria counts were quantified using aerobic colony forming units (CFU) obtained from plate counts utilizing Petrifilm available from 3M (St. Paul, Minn.). The results of the experiment are presented in Tables 18, 19, and 20, with n.d. denoting where the value was too low to detect.

TABLE 18

| Time (h) | Control cell dry weight (g/L) | HCl pH treated cell dry weight (g/L) |
|---|---|---|
| 0 | 1.2 | 1.2 |
| 11 | 1.4 | 1.4 |
| 24 | 1.6 | 1.6 |
| 35 | 1.9 | 2.2 |
| 48 | 1.5 | 2.5 |
| 59 | 1.0 | 3.5 |
| 72 | n.d. | 4.0 |
| 83 | n.d. | 4.8 |
| 96 | n.d. | 5.1 |
| 107 | n.d. | 5.4 |
| 120 | n.d. | 5.7 |
| 131 | n.d. | 6.1 |
| 144 | n.d. | 6.1 |
| 155 | n.d. | 1.9 |
| 168 | n.d. | 1.8 |

TABLE 19

| Time (h) | Control bacteria to microalgae ratio | HCl pH treated bacteria to microalgae ratio |
|---|---|---|
| 12 | 1.81 | 2.07 |
| 24 | 4.71 | 1.83 |
| 36 | 10.67 | #N/A |
| 48 | 7.27 | 2.06 |
| 108 | n.d. | 2.21 |
| 144 | n.d. | 2.44 |
| 168 | n.d. | 2.97 |

TABLE 20

| Time (h) | Control bacteria count (CFU) | HCl pH treated bacteria count (CFU) |
|---|---|---|
| 0 | 7.00E+06 | 4.00E+04 |
| 24 | 4.00E+07 | 1.50E+07 |
| 48 | 9.00E+07 | 1.20E+08 |
| 72 | n.d. | 2.20E+08 |
| 96 | n.d. | 1.30E+08 |
| 120 | n.d. | 1.20E+08 |
| 144 | n.d. | 1.50E+08 |

The results from Table 18 show that the untreated culture crashed (i.e., majority of the microalgae cells died) before reaching 48 hours after the transfer. The cell dry weight of the pH treated culture continued to increase for 144 hours, reaching a concentration of over 5 g/L, and then eventually crashed after 168 hours following a partial harvest of the microalgae culture. The results in Table 19 also show that the bacteria to microalgae ratio quickly increased in the first 48 hours in the untreated culture, but remained low in the pH treated culture through 108 hours before slowly increasing. The bacterial attachment in the pH treated culture was visually observed under a microscope to drop from about 50% to under 10% within 12 hours, and remained below 10% for over 100 hours before rapidly increasing and resulting in the crash of the culture. As shown in Table 20, the total bacteria live count of the pH treated culture immediately following treatment was approximately 2 logs lower than the untreated culture, and remained lower than the untreated culture for 24 hours.

Additionally, the untreated culture was visually observed under a microscope to contain more clumping of the algal cells than the pH treated culture. Both cultures were analyzed using qPCR to determine the bacteria population composition periodically over the life of the cultures, and the results showed that the cultures differed in the bacteria present, particularly *Cytophaga* sp. was detected in the untreated culture only. The data from these cultures demonstrates that such a pH treatment is effective in extending the productive life of a culture of microalgae with a high level of bacteria attachment, and that such a pH treatment is capable of reducing the % of bacteria attachment and lowers the total live bacteria count.

Example 14

This experiment was conducted to determine the effectiveness of a pH treatment in a microalgae culture that has a detectable concentration of bacteria known to attach to and negatively affect microalgae. A sample of a culture of *Chlorella* grown in mixotrophic conditions using acetic acid/pH-auxostat system operating with a residual acetate concentration in the range of 100-2500 ppm (i.e., first acid) as the organic carbon source and natural sunlight was pH treated using HCl (i.e., second acid) and NaOH as described in the previous examples to lower the culture pH from 7.5 to 3.5, maintain the culture pH at 3.5 for 15 minutes, and raise the culture pH to 7.5. Another sample was taken from the same *Chlorella* culture, but was not pH treated. After six days, the untreated sample showed bacteria attachment, and the qPCR probe developed for *Vampirovibrio chlorellavorus* was used to detect the levels in the treated and untreated culture. The results showed that the concentration of *Vampirovibrio chlorellavorus* in the untreated culture was approximately twice as high as in the treated culture, demonstrating the effectiveness of such a pH treatment against bacteria that has been observed to attach to and lyse microalgae.

Example 15

This experiment was conducted to determine the effect of different culture pH levels on the growth of *Chlorella*. Duplicate 100 ml flasks of axenic cultures of *Chlorella* were adjusted to initial pH levels of 2.5, 3.5, 4.5, 5.5, 6.5, 7.0, 7.5, 8.5, 9.5, and 10.5. The culture pH was adjusted using either hydrochloric acid (HCl) or sodium hydroxide (NaOH). All flask cultures were fed 1.00 mL of 240 g/L concentration sodium acetate (salt of acetic acid) daily. Samples of the flask culture were taken initially and every other day over a six day period (144 hours). The results of the cell dry weight (g/L) analysis are presented in Table 21, with n.d. denoting where a value was too low to be detected. It was noted during the experiment that the cultures with the higher initial pH values (i.e., 6.5 and above) equilibrate to about 7.5 within 24 hours, and to about 8.2 within 48 hours, while the lower initial pH values (i.e., below 6.5) were able to maintain the initial pH value for at least 24 hours. All flasks were able to maintain a pH value within a tolerance of 0.15 (+/−) for at least 3 hours.

TABLE 21

| Time (h) | Cell Dry Weight (g/L) of *Chlorella* by initial culture pH | | | | | | | | |
|---|---|---|---|---|---|---|---|---|---|
|  | 2.5 | 3.5 | 4.5 | 5.5 | 6.5 | 7.5 | 8.5 | 9.5 | 10.5 |
| 0 | 0.6 ± 0.0 | 0.6 ± 0.1 | 0.6 ± 0.0 | 0.6 ± 0.0 | 0.6 ± 0.0 | 0.6 ± 0.0 | 0.6 ± 0.0 | 0.6 ± 0.0 | 0.6 ± 0.0 |
| 24 | 0.5 ± 0.0 | 0.5 ± 0.0 | 0.5 ± 0.0 | 0.6 ± 0.0 | 0.8 ± 0.1 | 0.6 ± 0.3 | 0.8 ± 0.0 | 0.8 ± 0.0 | 0.9 ± 0.0 |
| 48 | 0.5 ± 0.0 | 0.5 ± 0.1 | 0.4 ± 0.1 | 0.6 ± 0.0 | 1.8 ± 0.2 | 1.7 ± 0.2 | 2.4 ± 0.2 | 1.2 ± 0.1 | 1.4 ± 0.1 |
| 96 | n.d. | n.d. | n.d. | 0.4 ± 0.0 | 4.3 ± 0.2 | 4.4 ± 0.0 | 4.2 ± 0.0 | 4.3 ± 0.2 | 4.3 ± 0.1 |
| 144 | n.d. | n.d. | n.d. | n.d. | 6.0 ± 0.1 | 6.0 ± 0.0 | 6.0 ± 0.4 | 6.1 ± 0.1 | 6.1 ± 0.1 |

The results in Table 21 show that the cell dry weight did not increase over time for cultures at a pH of 5.5 or lower, indicating that productive *Chlorella* cultures should be cultured at a pH above 5.5. The cultures at pH of 6.5 and above showed productive growth beginning at 48 hours after inoculation. The results also showed that the *Chlorella* was able to survive to some degree at pH values of 5.5 and lower.

Aspects of the Invention

In one non-limiting embodiment of the invention, a method of culturing microalgae comprises: preparing an open culture with organic carbon in a first bioreactor comprising bacteria and a population of selected microalgae in the presence of a growth sustaining amount of a first acid and a first pH value in the range of 5.5-10.5, the first acid comprising an acid with a pKa value in water in the range of 0-12; contacting the culture with a second acid, wherein a substantial portion of the second acid is made up of at least one acid other than the first acid, such that the pH of the culture is reduced to a second pH value greater than 0 and equal to or less than the pKa value of the first acid; maintaining the culture at the second pH value for a period of at least 5 minutes; and contacting the culture with a base, such that the pH of the culture is raised above the pKa value of the first acid.

In another non-limiting embodiment of the invention, a method of culturing microalgae comprises: preparing an open culture with organic carbon in a first bioreactor comprising bacteria and a population of selected microalgae in the presence of a growth sustaining amount of a first acid comprising an acid with a pKa value in water in the range of 0-12, and a first pH value of 1.25 to 2 times the pKa value of the first acid; contacting the culture with a second acid, wherein a substantial portion of the second acid is made up of at least one acid other than the first acid, such that the pH of the culture is reduced to a second pH value greater than 0 and equal to or less than the pKa value of the first acid; maintaining the culture at the second pH value for a period of at least 5 minutes; and contacting the culture with a base, such that the pH of the culture is raised to within 40% of the first pH value range.

In some embodiments, the steps of contacting the culture with a second acid, maintaining the culture at a second pH, and contacting the culture with a base may be repeated. In further embodiments, the steps may be repeated at least two times. In additional further embodiments, the steps may be repeated 2-14 days after the culture pH is raised using the base.

In another non-limiting embodiment of the invention, a method of culturing microalgae comprises: preparing an open culture with organic carbon in a first bioreactor comprising bacteria and a population of selected microalgae in the presence of a growth sustaining amount of a first acid and a first pH value in the range of 5.5-10.5, the first acid comprising an acid with a pKa value in water in the range of 0-12; removing a first fraction of the culture comprising bacteria and microalgae from the first bioreactor; contacting the first fraction of the culture with a second acid, wherein a substantial portion of the second acid is made up of at least one acid other than the first acid, such that the pH of the first fraction of the culture is reduced to a second pH value greater than 0 and equal to or less than the pKa value of the first acid; maintaining the first fraction of the culture at the second pH value for a period of at least 5 minutes; contacting the first fraction of the culture with a base, such that the pH of the first fraction of the culture is raised to above the pKa value of the first acid; and returning the first fraction of the culture to the first bioreactor, wherein the first fraction of the culture is mixed with the culture in the first bioreactor.

In another non-limiting embodiment of the invention, a method of culturing microalgae comprises: preparing an open culture with organic carbon in a first bioreactor comprising bacteria and a population of selected microalgae in the presence of a growth sustaining amount of a first acid comprising an acid with a pKa value in water in the range of 0-12, and a first pH value of 1.25 to 2 times the pKa value of the first acid; removing a first fraction of the culture comprising bacteria and microalgae from the first bioreactor; contacting the first fraction of the culture with a second acid, wherein a substantial portion of the second acid is made up of at least one acid other than the first acid, such that the pH of the first fraction of the culture is reduced to a second pH value greater than 0 and equal to or less than the pKa value of the first acid; maintaining the first fraction of the culture at the second pH value for a period of at least 5 minutes; contacting the first fraction of the culture with a base, such that the pH of the first fraction of the culture is raised to within 40% of the first pH value range; and returning the first fraction of the culture to the first bioreactor, wherein the first fraction of the culture is mixed with the culture in the first bioreactor.

In some embodiments, the steps of removing the first fraction, contacting the first fraction of the culture with a second acid, maintaining the first fraction of the culture at a second pH, contacting the first fraction of the culture with a base, and returning the first fraction of the culture to the first bioreactor may be repeated. In further embodiments, the steps may be repeated at least two times. In additional further embodiments, the steps may be repeated on a continuous basis. In additional further embodiments, the steps may be repeated 12-48 hours after the first fraction of the culture is returned to the first bioreactor.

In some embodiments, the first acid may provide a source of organic carbon to the microalgae sufficient for mixotrophic or heterotrophic growth. In some embodiments, the first acid may be present in a primarily dissociated form at the first pH. In some embodiments, the first acid may be present in a primarily undissociated form at the second pH. In some embodiments, the first acid comprises at least one selected from the group consisting of acetic acid, pyruvic acid, propionic acid, palmitic acid, and malic acid. In further embodiments, the first acid may be acetic acid and a concentration of acetate in the culture is maintained at a level less than 7.5 g/L during the culturing.

In some embodiments, the second acid may comprise an acid with a pKa in water of less than −2. In some embodiments, the second acid may comprise at least one from the group consisting of sulphuric acid, hydrochloric acid, and muriatic acid. In some embodiments, the base may comprise at least one from the group consisting of sodium hydroxide, potassium hydroxide, and calcium hydroxide.

In some embodiments, the culture may be maintained at the second pH value for about 5 to 210 minutes. In some embodiments, the culture may be maintained at the second pH value for about 5 to 15 minutes. In some embodiments, the culture may be maintained at the second pH value for about 15 to 60 minutes. In some embodiments, the culture may be maintained at the second pH value for about 60 to 120 minutes. In some embodiments, the culture may be maintained at the second pH value for about 120 to 180 minutes.

In some embodiments, the first pH may be in the range of 6.5-8.5. In some embodiments, the second pH value may be in the range of 1-5. In some embodiments, the second pH value may be in the range of 3-4.

In some embodiments, the acetic acid present in the culture may diffuse through the cell membrane of the bacteria when the second pH value is equal to or less than the pKa value of the acetic acid and does not form an acetate concentration greater than 7.5 g/L in the culture. In some embodiments, the intracellular pH value of the bacteria decreases when the second pH value is equal to or less than the first acid pKa value.

In some embodiments, the bacteria may comprise a detectable amount of at least one of *Vampirovibrio chlorellavorus* and *Cytophaga* sp. In some embodiments, the method may further comprise determining a first live bacteria count of the culture before contact with the second acid; and determining a second live bacteria count of the culture after the culture pH is raised with the base. In further embodiments, the second live bacteria count may be reduced by at least 1 log as compared to the first live bacteria count within 48 hours or less. In further embodiments, the second live bacteria count may be reduced by 1-4 logs as compared to the first live bacteria count within 48 hours or less.

In some embodiments, contact with the second acid may occur when a % of bacteria attached to the microalgae as observed under a microscope is about 50% or less. In some embodiments, a % of bacteria attached to the microalgae as observed under a microscope may be reduced by at least 50% in 24 hours or less after the culture pH is raised with the base. In some embodiments, a % of bacteria attached to the microalgae as observed under a microscope may be reduced to less than 5% in 48 hours or less after the pH is raised with the base. In some embodiments, a % of bacteria attached to the microalgae as observed under a microscope may not increase for at least 24 hours after the culture pH is raised with the base. In some embodiments, a % of bacteria attached to the microalgae as observed under a microscope may not increase for at least 48 hours after the culture pH is raised with the base.

In some embodiments, the method may further comprise analyzing the culture before contact with the second acid to determine a first live bacteria population composition; and analyzing the culture after the culture pH is raised with the base to determine a second live bacteria population composition. In some embodiments, the second live bacteria population composition may have less of at least one bacteria selected from the group consisting of *Vampirovibrio chlorellavorus* and *Cytophaga* sp. than the first live bacteria population composition.

In some embodiments, the method may further comprise concentrating the culture in the range of 2-25% solids prior to contacting the culture with the second acid. In some embodiments, the method may further comprise transferring the culture to a second bioreactor after the culture is contacted with the second acid. In some embodiments, the method may further comprise transferring the culture to a second bioreactor after the culture is contacted with the base.

In some embodiments, the first bioreactor may be disposed outdoors. In some embodiments, the second bioreactor may be disposed outdoors.

In some embodiments, the method may further comprise culturing the microalgae in phototrophic conditions after the culture pH is raised with the base. In some embodiments, the method may further comprise culturing the microalgae in mixotrophic conditions after the culture pH is raised with the base. In some embodiments, the method may further comprise culturing the microalgae in heterotrophic conditions after the culture pH is raised with the base.

In some embodiments, the method may further comprise supplying the culture with photosynthetically active radiation (PAR). In some embodiments, the culture may comprise a volume in the range of 1,000-500,000 liters. In some embodiments, the culture may further comprise separating at least a portion of the bacteria from the microalgae, and removing the separated bacteria from the culture prior to contacting the culture with the second acid. In some embodiments, the method may further comprise adding a probiotic culture of bacteria to the culture after the culture pH is raised with the base. In some embodiments, the method may further comprise removing foam from the culture after the culture pH is raised with the base.

In some embodiments, the cell dry weight density of the culture may be 0.5-5 g/L prior to contacting the culture with the second acid. In some embodiments, the culture may be diluted to a cell density less than or equal to 2 g/L after the culture pH is raised with the base. In some embodiments, substantially the entire culture may be contacted with the second acid and base.

In some embodiments, the method may further comprise continuing the growth of the microalgae for at least 48 hours longer than the growth in an untreated control. In some embodiments, a productive life of the microalgae in the culture may be at least twice as long as a productive life of an untreated control.

In some embodiments, the microalgae may comprise green algae. In some embodiments, the green algae may comprise at least one selected from the group consisting of *Chlorella* and *Chlamydomonas*.

In another non-limiting embodiment of the invention, a method of culturing microalgae may comprise: preparing an open culture with organic carbon in a first bioreactor comprising bacteria and a population of selected microalgae at a first pH value in the range of 5.5-10.5; contacting the culture with an acid with a pKa value in water in the range of 0-12, such that the pH of the culture is reduced to a second pH value greater than 0 and equal to or less than the pKa value of the acid; maintaining the culture at the second pH value for a period of at least 5 minutes; and contacting the culture with a base, such that the pH of the culture is raised above the pKa value of the acid.

In another non-limiting embodiment of the invention, a method of culturing microalgae may comprise: preparing an open culture with organic carbon comprising bacteria and a population of selected microalgae in the presence of a growth sustaining amount of a first acid and a first pH value in the range of 5.5-10.5 in a microalgae culturing means, the first acid comprising an acid with a pKa value in water in the range of 0-12; contacting the culture with a pH reducing means, such that the pH of the culture is reduced to a second pH value greater than 0 and equal to or less than the pKa value of the first acid; maintaining the culture at the second pH value for a period of at least 5 minutes; and contacting the culture with a pH raising means, such that the pH of the culture is raised above the pKa value of the first acid.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). All provided ranges of values are intended to include the end points of the ranges, as well as values between the end points.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims and/or aspects appended hereto as permitted by applicable law.

What is claimed is:

1. A method of reducing bacterial contamination in a microalgae culture, comprising:
   a. preparing in an open culture in a first bioreactor a microalgae culture having or suspected of containing a contaminating population of bacteria, in the presence of a microalgal-growth sustaining amount of a first acid, wherein said first acid:
      (i) is a carboxylic acid having a pKa in water of 0-12, and comprising one or more of acetic acid, pyruvic acid, propionic acid, palmitic acid, and malic acid, and
      (ii) wherein when the first acid is acetic acid, it provides the microalgae culture with a maintained amount of 7.5 g/L or less of the conjugate base of said first acid, thereby providing the microalgae culture with a first pH of 5.5-10.5;
   b. contacting the microalgae culture with a second acid having a pKa equal to or less than the pKa of the first acid, wherein a substantial portion of the second acid is made up of at least one acid other than the first acid, thereby reducing the pH of the culture to a second pH greater than 0;
   c. maintaining the microalgae culture at the second pH value for a period of at least 5 minutes, thereby reducing the population of viable bacteria in the microalgae culture; and
   d. contacting the microalgae culture with a base, such that the pH of the culture is raised above the pKa value of the first acid, thereby providing said microalgae culture having a reduced bacterial contamination.

2. The method of claim 1, further comprising repeating steps b, c, and d a least two times.

3. The method of claim 2 wherein steps b, c, and d are repeated 2-14 days after the culture pH is raised using the base.

4. The method of claim 1, wherein the first acid provides a source of organic carbon to the microalgae sufficient for mixotrophic or heterotrophic growth.

5. The method of claim 1, wherein the first acid is present in a primarily dissociated form at the first pH.

6. The method of claim 1, wherein the first acid is one or more carboxylic acid selected from the group consisting of acetic acid, pyruvic acid, propionic acid, palmitic acid, and malic acid.

7. The method of claim 6, wherein the first acid is acetic acid, wherein the conjugate base is acetate, and wherein the method comprises maintaining the acetate in the microalgae culture in an amount less than 7.5 g/L.

8. The method of claim 1, wherein the second acid comprises an acid with a pKa in water of less than −2.

9. The method of claim 8, wherein the second acid comprises at least one acid selected from the group consisting of sulphuric acid and hydrochloric acid.

10. The method of claim 1, wherein the base comprises at least one base selected from the group consisting of sodium hydroxide, potassium hydroxide, and calcium hydroxide.

11. The method of claim 1, wherein the culture is maintained at the second pH for about 5 to 210 minutes.

12. The method of claim 11, wherein the culture is maintained at the second pH for about 5 to 15 minutes.

13. The method of claim 11, wherein the culture is maintained at the second pH for about 15 to 60 minutes.

14. The method of claim 1, wherein the first pH is in the range of 6.5-8.5.

15. The method of claim 1, wherein the second pH is in the range of 3-4.

16. The method claim 1, further comprising concentrating the culture in the range of 2-25% solids prior to said contacting the culture with the second acid.

17. The method claim 1, further comprising separating at least a portion of the bacteria from the microalgae in the culture, and removing the separated bacteria from the microalgae culture prior to said contacting the microalgae culture with the second acid.

18. The method of claim 1, wherein the microalgae culture has a cell dry weight density of 0.5 g/L prior to said contacting the microalgae culture with the second acid.

19. The method of claim 1, wherein the microalgae culture is diluted to a cell density less than or equal to 2 g/L after the microalgae culture pH is raised with the base.

20. The method of claim 1, wherein the microalgae comprise at least one green algae selected from the group consisting of *Chlorella* and *Chlamydomonas*.

* * * * *